US006996951B2

(12) United States Patent
Smith et al.

(10) Patent No.: US 6,996,951 B2
(45) Date of Patent: Feb. 14, 2006

(54) FLEXIBLE MULTI-COMPARTMENT CONTAINER WITH PEELABLE SEALS AND METHOD FOR MAKING SAME

(75) Inventors: Steven L. Smith, Lake Forest, CA (US); Ward Barney, Mission Viejo, CA (US); Noel Gharbian, Glendale, CA (US); Douglas G. Harvey, Mission Viejo, CA (US); Mark R. Mclonis, Playa Del Rey, CA (US); Christopher D. Peara, Milwaukee, WI (US); Scott L. Pool, Laguna Hills, CA (US); Giuseppe Sacca, Laguna Niguel, CA (US); Thomas R. Sakaguchi, Irvine, CA (US); Sharilyn J. Sandberg, Rossmoor, CA (US); William V. Walter, Huntington Beach, CA (US); Nicholas Chung-Hui Wu, Irvine, CA (US); Walter A. York, Mission Viejo, CA (US); H. Theodore Young, Irvine, CA (US); William A. Sperko, Yorba Linda, CA (US); Robert E. Turner, San Clemente, CA (US); William B. Ray, Anaheim, CA (US)

(73) Assignee: B. Braun Medical Inc., Bethlehem, PA (US)

( * ) Notice: Subject to any disclaimer, the term of this patent is extended or adjusted under 35 U.S.C. 154(b) by 0 days.

(21) Appl. No.: 10/664,643

(22) Filed: Sep. 17, 2003
(Under 37 CFR 1.47)

(65) Prior Publication Data
US 2004/0068960 A1 Apr. 15, 2004

Related U.S. Application Data

(60) Division of application No. 10/112,325, filed on Mar. 29, 2002, now Pat. No. 6,846,305, which is a continuation of application No. 09/247,997, filed on Feb. 10, 1999, now Pat. No. 6,468,377, which is a division of application No. 08/967,692, filed on Nov. 12, 1997, now Pat. No. 5,910,138, which is a continuation-in-part of application No. 08/837,927, filed on Apr. 11, 1997, now Pat. No. 5,944,709, which is a continuation-in-part of application No. 08/647,583, filed on May 13, 1996, now abandoned.

(51) Int. Cl.
*B65B 55/02* (2006.01)
(52) U.S. Cl. ............................. 53/425; 53/469; 53/477
(58) Field of Classification Search ................. 53/412, 53/425, 426, 469, 477; 493/189, 190, 210, 493/212, 213; 206/219, 220, 221; 604/85, 604/87, 410
See application file for complete search history.

(56) References Cited

U.S. PATENT DOCUMENTS

| | | |
|---|---|---|
| 2,335,978 A | 12/1943 | Vogt |
| 2,483,636 A | 10/1949 | Hardesty |
| 2,564,656 A | 8/1951 | Chedister |
| 2,663,298 A | 12/1953 | Rose |
| 3,074,544 A | 1/1963 | Bollmeier et al. |
| 3,149,017 A | 9/1964 | Ehrreich et al. |
| 3,254,828 A | 6/1966 | Lerner |
| 3,257,072 A | 6/1966 | Reynolds |
| 3,520,471 A | 7/1970 | Faust |
| 3,545,671 A | 12/1970 | Ross |
| 3,554,256 A | 1/1971 | Anderson |
| 3,608,709 A | 9/1971 | Pike |
| 3,749,620 A | 7/1973 | Montgomery |
| 3,756,389 A | 9/1973 | Firth |
| 3,794,490 A | 2/1974 | Nerwin |
| 3,809,224 A | 5/1974 | Greenwood |
| 3,847,279 A | 11/1974 | Montgomery |
| 3,865,667 A | 2/1975 | Ferrari |
| 3,882,259 A | 5/1975 | Nohara et al. |
| 3,911,640 A | 10/1975 | Rausing |
| 3,946,871 A | 3/1976 | Sturm |
| 3,964,604 A | 6/1976 | Prenntzell |
| 3,985,135 A | 10/1976 | Carpenter et al. |
| 4,010,786 A | 3/1977 | Aguettant et al. |
| 4,183,434 A | 1/1980 | Watt |

| | | |
|---|---|---|
| 4,198,972 A | 4/1980 | Herb |
| 4,223,512 A | 9/1980 | Buchner |
| 4,224,367 A | 9/1980 | Scholle |
| 4,236,652 A | 12/1980 | Beguhn |
| 4,252,846 A | 2/1981 | Romesberg et al. |
| 4,270,533 A | 6/1981 | Andreas |
| 4,284,672 A | 8/1981 | Stillman |
| 4,375,145 A | 3/1983 | Mosse et al. |
| 4,396,382 A | 8/1983 | Goldhaber |
| 4,396,383 A | 8/1983 | Hart |
| 4,401,214 A | 8/1983 | Kleckers |
| 4,402,402 A | 9/1983 | Pike |
| 4,409,775 A | 10/1983 | Brody et al. |
| 4,410,321 A | 10/1983 | Pearson et al. |
| 4,417,607 A | 11/1983 | Scholle et al. |
| 4,432,763 A | 2/1984 | Manschot |
| 4,452,030 A | 6/1984 | Inada |
| 4,458,811 A | 7/1984 | Wilkinson |
| 4,465,488 A | 8/1984 | Richmond et al. |
| 4,467,588 A | 8/1984 | Carveth |
| 4,484,920 A | 11/1984 | Kaufman et al. |
| 4,496,046 A | 1/1985 | Stone et al. |
| 4,507,114 A | 3/1985 | Bohman et al. |
| 4,519,499 A | 5/1985 | Stone et al. |
| 4,528,220 A | 7/1985 | Hwo |
| 4,530,202 A | 7/1985 | Powell et al. |
| 4,548,023 A | 10/1985 | Danby et al. |
| 4,566,251 A | 1/1986 | Spisak et al. |
| 4,588,554 A | 5/1986 | Kaartinen et al. |
| 4,600,613 A | 7/1986 | Yoshida |
| 4,602,910 A | 7/1986 | Larkin |
| 4,608,043 A | 8/1986 | Larkin |
| 4,610,684 A | 9/1986 | Knox et al. |
| 4,614,267 A | 9/1986 | Larkin |
| 4,619,650 A | 10/1986 | Wisdom |
| 4,622,032 A | 11/1986 | Katsura et al. |
| 4,629,080 A | 12/1986 | Carveth |
| 4,693,052 A | 9/1987 | Rebmann et al. |
| 4,702,963 A | 10/1987 | Phillips et al. |
| 4,711,359 A | 12/1987 | White et al. |
| 4,731,053 A | 3/1988 | Hoffman |
| 4,742,667 A | 5/1988 | Muller et al. |
| 4,770,295 A | 9/1988 | Carveth et al. |
| 4,803,102 A | 2/1989 | Raniere et al. |
| 4,805,767 A | 2/1989 | Newman |
| 4,813,210 A | 3/1989 | Masuda et al. |
| 4,837,084 A | 6/1989 | Warren |
| 4,874,656 A | 10/1989 | Rantanen |
| 4,910,085 A | 3/1990 | Raniere et al. |
| 4,910,147 A | 3/1990 | Bacehowski |
| 4,961,495 A | 10/1990 | Yoshida et al. |
| 4,965,108 A | 10/1990 | Biel et al. |
| 4,965,109 A | 10/1990 | Tucker et al. |
| 4,969,915 A | 11/1990 | Hatanaka et al. |
| 4,979,347 A | 12/1990 | Shibauchi et al. |
| 4,992,247 A | 2/1991 | Foti |
| 4,994,056 A | 2/1991 | Ikeda |
| 5,007,232 A | 4/1991 | Caudill |
| 5,011,719 A | 4/1991 | Gehrke et al. |
| 5,014,494 A | 5/1991 | George |
| 5,069,017 A | 12/1991 | Fabricius |
| 5,071,686 A | 12/1991 | Genske et al. |
| 5,114,004 A | 5/1992 | Isono et al. |
| 5,129,212 A | 7/1992 | Duffey et al. |
| 5,131,760 A | 7/1992 | Framer |
| 5,176,634 A | 1/1993 | Smith et al. |
| 5,207,509 A | 5/1993 | Herbert |
| 5,209,347 A | 5/1993 | Fabisiewicz et al. |
| 5,240,525 A | 8/1993 | Percec et al. |
| 5,257,985 A | 11/1993 | Puhl |
| 5,259,844 A | 11/1993 | Bilstad et al. |
| 5,267,646 A | 12/1993 | Inoue et al. |
| 5,287,961 A | 2/1994 | Herran |
| 5,306,269 A | 4/1994 | Lewis et al. |
| 5,324,233 A * | 6/1994 | Owensby et al. ........... 493/190 |
| 5,334,180 A | 8/1994 | Adolf et al. |
| 5,423,421 A | 6/1995 | Inoue et al. |
| 5,425,447 A | 6/1995 | Farina |
| 5,431,496 A | 7/1995 | Balteau et al. |
| 5,458,244 A | 10/1995 | Emori |
| 5,462,526 A | 10/1995 | Barney et al. |
| 5,484,633 A | 1/1996 | Murschall et al. |
| 5,487,940 A | 1/1996 | Bianchini et al. |
| 5,492,534 A * | 2/1996 | Athayde et al. ............ 604/141 |
| 5,493,845 A | 2/1996 | Adolf et al. |
| 5,496,302 A | 3/1996 | Minshall et al. |
| 5,501,887 A | 3/1996 | Tanaka et al. |
| 5,514,123 A | 5/1996 | Adolf et al. |
| 5,520,975 A | 5/1996 | Inoue et al. |
| 5,770,003 A | 6/1998 | Tabaroni et al. |
| 6,017,598 A | 1/2000 | Kreischer et al. |

FOREIGN PATENT DOCUMENTS

| | | |
|---|---|---|
| DE | 24 53 263 A1 | 5/1976 |
| EP | 0 692 364 A1 | 1/1996 |
| JP | 385038 | 8/1991 |
| JP | 626563 | 4/1994 |
| JP | 2675049 | 7/1997 |
| WO | WO 94/08852 | 4/1994 |
| WO | WO 98/13191 | 4/1998 |

OTHER PUBLICATIONS

Inoue, "A New Package for a Kit Product: A Multiple Chamber Plastic Bag Packaging parenteral Powder Drug and Diluent," PDA Asian Symposium and Exhibit, Tokyo, Japan 1994, 7 pages.

McGaw, Inc., "Discussion Guide," (DUPLEX™ Focus Groups), Oct. 24, 1994, 3 pages.

Engineering Drawing No. S6272 entitled DUPLEX Container, Oct. 1994, 1 page.

* cited by examiner

*Primary Examiner*—Louis Huynh
(74) *Attorney, Agent, or Firm*—Christie Parker & Hale, LLP

(57) ABSTRACT

A flexible container is provided for the storage and administration of medical solutions. The container incorporates a transparent front sheet made from a planar layer of a polymer and an opposing rear sheet. The rear sheet is made from a planar laminate layer. The front and rear sheets are sealed together along a common peripheral edge to form a volume enclosure. The volume enclosure is constructed of materials having high oxygen and moisture barrier properties which allows the container thermoplastic to be stored for extended periods of time without degrading the contents. The volume enclosure is then inflated with a pressurized gas to permanently stretch the front and rear sheets outwardly and to thereby increase the volume capacity of the container. An alternative embodiment of the container incorporates multiple compartments, separated by peelable seals, for containing a diluent and a medicament. The seals are ruptured by manipulation of the container to thereby mix the contents together for delivery through standard IV arrangement to a patient.

16 Claims, 8 Drawing Sheets

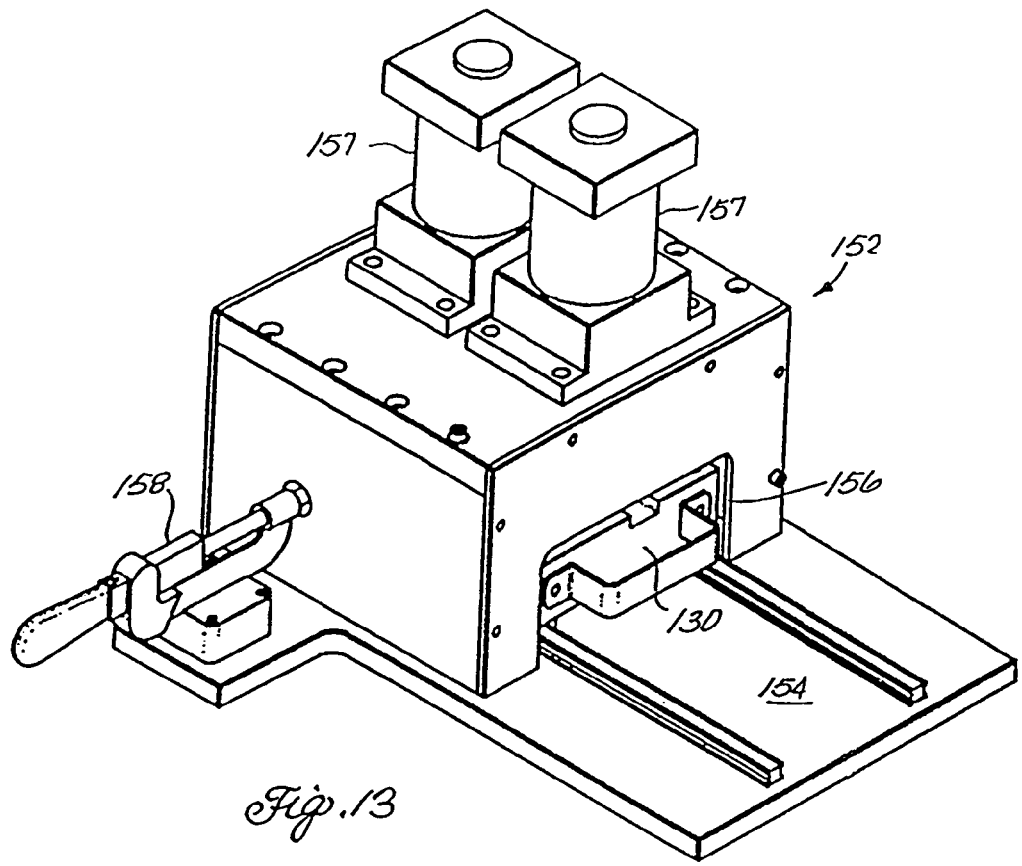
Fig. 13
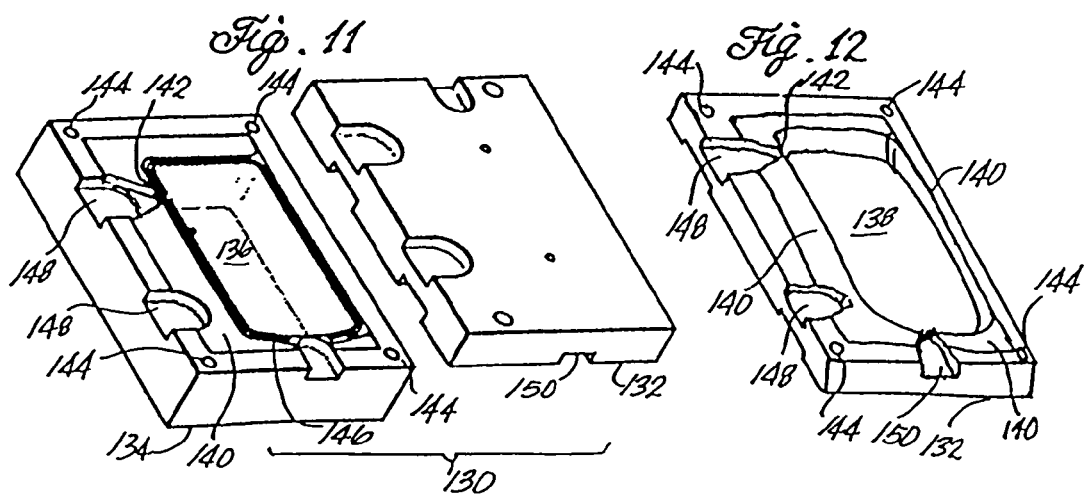
Fig. 11
Fig. 12

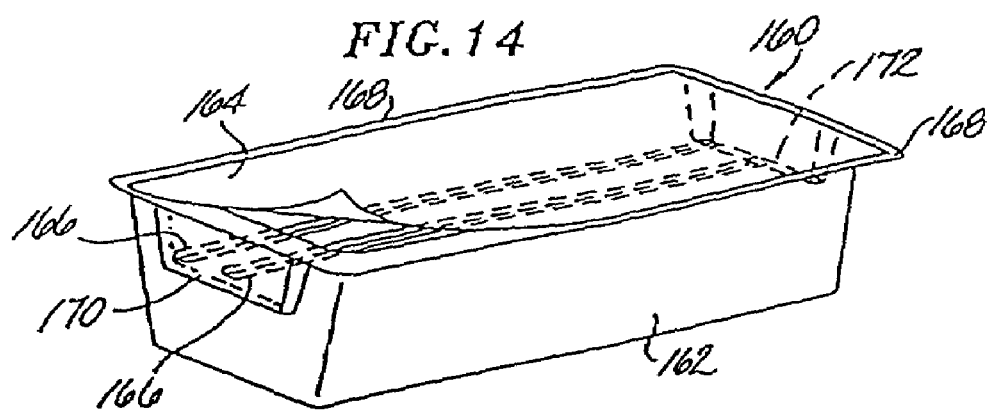
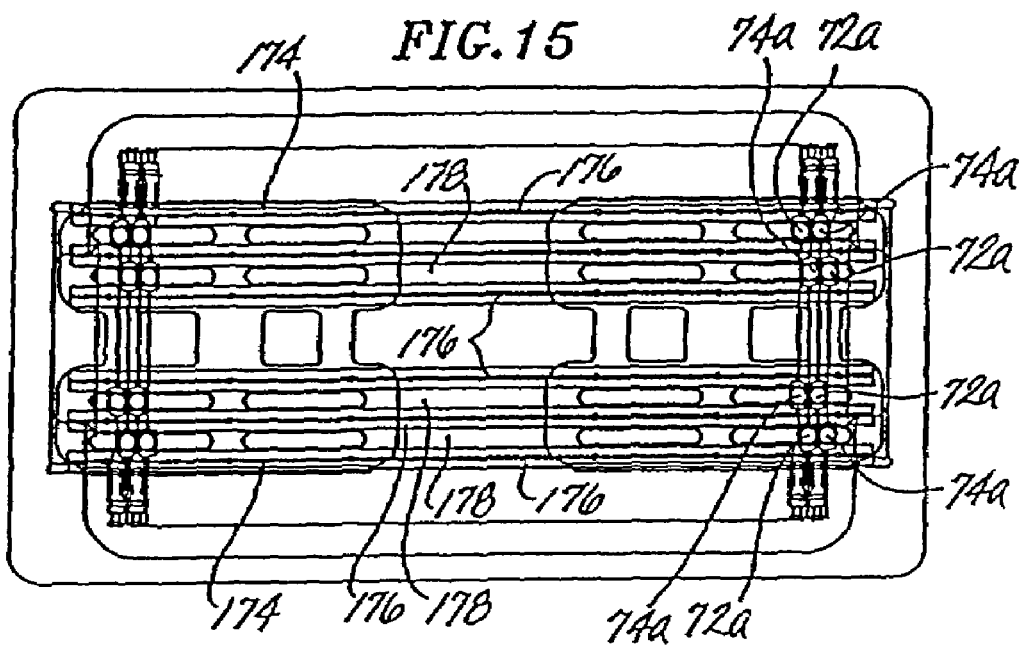
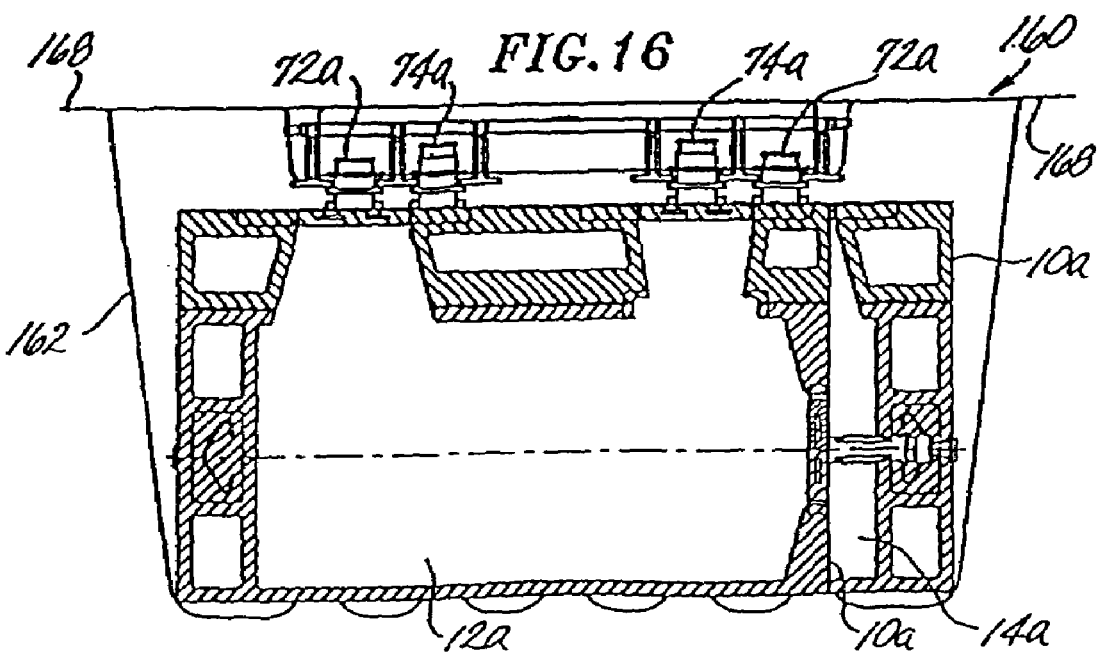

US 6,996,951 B2

FLEXIBLE MULTI-COMPARTMENT CONTAINER WITH PEELABLE SEALS AND METHOD FOR MAKING SAME

CROSS-REFERENCE TO RELATED APPLICATIONS

This is a division of application Ser. No. 10/112,325 filed Mar. 29, 2002 now U.S. Pat. No. 6,846,305, which is a continuation application of application Ser. No. 09/247,997 filed Feb. 10, 1999, now U.S. Pat. No. 6,468,377, which is a divisional of application Ser. No. 08/967,692 filed Nov. 12, 1997, now U.S. Pat. No. 5,910,138, which is a continuation-in-part of application Ser. No. 08/837,927 filed Apr. 11, 1997, now U.S. Pat. No. 5,944,709, which is a continuation-in-part of application Ser. No. 08/647,583 filed May 13, 1996, now abandoned. The present invention is also related to co-pending application entitled "FLEXIBLE MULTIPLE COMPARTMENT MEDICAL CONTAINER WITH PREFERENTIALLY RUPTURABLE SEALS", now U.S. Pat. No. 6,117,123. All of these applications are commonly owned by the Assignee of the present invention, the entire disclosures of which are expressly incorporated herein by reference.

FIELD OF THE INVENTION

The present invention relates to flexible, sterile containers, for storing and administering medical solutions in a sterile environment. More particularly, the present invention relates to flexible medical containers for storing and administering IV solutions and having sides which are permanently stretched to enlarge their storage capacity.

BACKGROUND OF THE INVENTION

Various medical solutions are commonly administered intravenously (via IV) from sterile containers to patients. These solutions may include any medical type fluids, such as replacement body fluids and even solutions containing a medicament (drug). Common packaging for the storage and administration of these solutions includes flexible containers having a compartment for storing the solution. An outlet port is coupled to the compartment for administration and delivery of the solution to the patient through a standard IV arrangement.

Oftentimes, medical solutions consist of a mixed combination of a liquid diluent, e.g., an aqueous dextrose or NaCl solution, and a liquid medicament. Desirably, the medicament and diluent are stored separately in the container under aseptic conditions and are not mixed together until immediately prior to use so as to prevent degradation of the final product. Packaging of the diluent and medicament is often further complicated by the character of the medicament which may be in liquid form and, thus, susceptible to hydraulic pressure on the container, as well as degradation under light or oxygen exposure.

Accordingly, various such medicaments which become unstable with time in solution have typically been separately stored in gas-impermeable vials, containers, or the like prior to their use. Before being administered to a patient, medicaments stored in this fashion must be mixed, or diluted in, physiological solutions or diluents which are also preserved separately. While able to maintain medicament sterility and effectiveness, separate component storage is cumbersome and involves the risk of bacteriological contamination during handling, mixing, and subsequent administration to a patient. Accordingly, medical containers have been developed which include compartments for storing unstable medicaments and compartments which contain diluent liquids. Immediately prior to IV administration to a patient, the components are placed in communication with one another so that the contents can be mixed together aseptically.

Multiple compartment containers, which allow separate storage of diluents and medicaments are known. Such containers are disclosed, for example, in U.S. Pat. No. 4,608,043 to Larkin, U.S. Pat. No. 5,176,634 to Smith et al. and U.S. Pat. No. 5,462,526 to Barney et al. U.S. Pat. Nos. 4,608,043, 5,176,634 and 5,462,526 are expressly incorporated herein in their entirety by reference. The compartments of the containers disclosed in the foregoing patents are separated from one another by peelable or frangible heat seals. The seals are ruptured by manipulation of the container so that the contents of the compartments can be mixed together to thereby form a solution which is delivered to the patient through a standard IV arrangement.

Solution containers on the market today are generally manufactured of materials comprising PVC plastic. PVC material is generally quite murky in aspect, making it difficult to inspect the contents of a container manufactured of such material. Consequently, inspecting such containers for leaks and moisture contamination is quite difficult. Inspection is further complicated when using multiple compartment containers, where there is a need to verify whether complete mixing of the medicament and diluent has taken place prior to administration to a patient. In addition, various hazardous chemicals are used in the manufacture of PVC material which must be disposed of in an environmentally safe manner. PVC containers must be carefully disposed of following their use, because PVC emits a toxic gas when incinerated and includes a toxic plasticizer that can leach into the surrounding environment if the container is buried in a landfill. This toxic plasticizer is also able to leach into IV solutions, making PVC containers unsuitable for use with several types of medical fluids, and particularly with liquid drugs.

These flexible containers are typically fabricated from a pair of opposing planar sheets which are mated together to form a body or shell. Forming a particular sized body results in a fixed volume capacity. Typically, the containers are fabricated to hold standardized volumes. This works well until a non standard volume is necessary. In this situation, one option is to utilize only a portion of the solution stored in a larger container. However, this option is expensive, wasteful and dangerous. The user must also be very careful to only use the desired quantity or prescription of the contained fluid. In addition, any remaining solution may require specialized disposal.

The containers are also typically fabricated to a predetermined overall outer size or a few common overall sizes. This is generally because the overall size of the container determines its volume capacity, and currently containers are provided in a relatively few predetermined volumes. In addition, the fabrication, handling and sterilization of these containers requires highly complex and expensive machinery. This machinery is designed, in part, to handle the overall dimensions of the container. It is therefore desirable to provide a medical container which has a standard overall outer size and has an enlarged volume capacity relative to the standard size. It is further desirable that the medical container be fabricated using the same machinery and handling equipment as that for standard size containers.

Similar to the single compartment containers, multi-compartment containers are typically constructed with predetermined compartment sizes. The diluent compartment is typically sized to hold a sufficient quantity of diluent to mix with the stored medicament and form a proper solution. The diluent compartment size is also based on a particular dosage or stored quantity of the medical solution. The volume of the diluent compartment may also be limited by the overall outer size of the container which must be constructed to fit the packaging and handling equipment. However, in some applications, it may be desirable to increase the quantity of diluent. Currently this is not possible or requires a second container of diluent. Alternatively, some applications may require additional medicament. It is therefore desirable to provide a multi-compartment medical container that has a standard overall outer size with standardized compartment volume capacities that can be permanently enlarged to increase the volume capacity of at least one of the compartments. It is further desirable that the container be manufactured to a predetermined overall size and configuration to facilitate manufacturing, sterilization and handling by the same machinery and processes.

SUMMARY OF THE INVENTION

The present invention provides a flexible medical container for storing medical solutions which is capable of being permanently enlarged to increase its storage capacity. The present invention also provides a flexible medical container for storing medical solutions and powders which is manufactured to a standardized overall size and optionally enlarged to increase its storage capacity. By providing a flexible container having a front sheet and a rear sheet which can be permanently stretched, the volume capacity of the container can be increased to a variety of sizes and shapes. By adding a simple, optional, enlarging step to the container manufacturing process, the volume enclosure of some containers may be enlarged while others may be kept at a generally standardized or non-enlarged capacity. This advantageously allows the present containers to be substantially fabricated, handled and administered using current methods and equipment.

In one aspect of the present invention, a flexible container for combined storage and administration of a medical fluid is provided. The flexible container includes a substantially transparent front sheet having a first surface area. The front sheet is constructed from a flexible planar layer of a polymer film. A rear sheet having a second surface area and being constructed from a flexible planar layer of a laminate is disposed opposing the front sheet. The front sheet and the rear sheet are sealably attached together along a common peripheral edge to form a volume enclosure. A port is supported along the common peripheral edge and fluidly connected with the volume enclosure. At least one of the front sheet and the rear sheet is permanently elongated to increase the storage capacity of the volume enclosure and thus, the container.

In another aspect of the present invention, the flexible container includes a substantially transparent front sheet having a first surface area. The front sheet is constructed from a flexible planar layer of a polypropylene-polyethylene copolymer blended with a styrene ethylene-butylene styrene thermoplastic elastomer. A similarly sized rear sheet having a second surface area is disposed opposing the front sheet. The rear sheet is constructed from a flexible planar layer of a laminate including an inner layer of a polypropylene-polyethylene copolymer blended with a styrene ethylene-butylene styrene thermoplastic elastomer. This inner layer is disposed facing the opposing front sheet. The rear sheet also includes an intermediate layer of an aluminum foil and an outer thermoplastic layer having a higher melting point than the inner layer. The front sheet and the rear sheet are sealably attached together along a portion of the common portion of the peripheral edge to form a volume enclosure.

A first peelable seal extends between a first side of the common peripheral edge and an opposing second side of the common peripheral edge. This first peelable seal joins the front sheet and the rear sheet together to form a first compartment within the volume enclosure for containing a diluent. A second peelable seal extends between the opposing first and second sides of the common peripheral edge. This second peelable seal joins the front sheet and the rear sheet together to form a second compartment for containing a medicament and a third outlet compartment. The second compartment is disposed between the first compartment and the outlet compartment.

An outlet port is supported along the common peripheral edge. The outlet port is fluidly connected to the outlet compartment. A diluent port is also supported along the common peripheral edge. The diluent port is fluidly connected with the first compartment through a break in the seal along the common peripheral edge. A medicament port is also supported along the common peripheral edge. A medicament port is fluidly connected with the second compartment through a second break in the seal along the common peripheral edge.

In yet a further aspect of the present invention, a method for forming a flexible container for combined storage and administration of medicaments and diluents for IV solutions is disclosed. The method includes the steps of providing a substantially transparent front sheet and a flexible and vapor impermeable rear sheet. The provided front sheet is constructed from a flexible planar layer of a polymer film. The rear sheet is constructed from a planar multi layer laminate. The front sheet and the rear sheet are sealed together along their common peripheral edge so as to define a volume enclosure.

The method also includes the steps of providing first and second sacrificial ports which are supported along a first side of the common peripheral edge and fluidly connected to the volume enclosure. The first sacrificial port is spaced apart from the second sacrificial port along this first side. The outlet port is supported along a second side of the common peripheral edge and is also fluidly connected to the volume enclosure.

The volume enclosure is expanded through inflation with a pressurized gas to permanently stretch at least the front sheet and to thereby increase the volume capacity of the container. The pressurized gas is then relieved from the expanded container. The permanently stretched volume enclosure is then filled with a second gas. The sacrificial ports and the outlet port are then capped to maintain the container in an expanded configuration.

After the container has been permanently expanded, each of the sacrificial ports may be removed. This step includes removing a portion of the first side along the common peripheral edge. The front sheet is then sealably attached to the rear sheet along the first side inwardly from the sacrificial ports to form a continuous permanent seal about the common peripheral edge.

In yet a further aspect of the present invention, a method for increasing the capacity of a flexible container for storage and administration of medical fluids is disclosed. The method includes providing a flexible container, such as the container of the present invention. The provided container includes a flexible planar front sheet opposing a flexible planar rear sheet along a common plane. The front sheet is sealably attached to the flexible rear sheet along a common peripheral edge to form a volume enclosure. A port is connected to the container and fluidly connected with the volume enclosure. The method includes the step of expanding the volume enclosure to permanently stretch at least the front sheet and thereby increase the volume capacity of the container.

The step of expanding the volume enclosure includes providing a multi-piece tool which is configured for receiving the volume enclosure. The tool includes a lower tool portion and an opposing upper tool portion. The lower tool portion has a lower planar edge surrounding a lower concave region. In a similar configuration, the upper tool portion has an upper concave region with surrounding upper planar edge. The lower and upper planar edges are generally opposed and configured to capture the common peripheral edge. The container is sandwiched between the tool with the rear sheet facing the lower concave region and the front sheet facing the upper concave region. The volume enclosure is then inflated with a pressurized gas to permanently stretch the front and rear sheets outwardly and against the respective concave regions of the tool. The volume enclosure is maintained inflated for a time sufficient to overcome substantial elastic rebounding.

In yet a further aspect of the present invention, a second method for forming a flexible container for combined storage and administration of medicaments and diluents for IV solutions is disclosed. The method includes providing a flexible and substantially transparent front sheet constructed from a planar layer of a polymer. A flexible and vapor impermeable rear sheet constructed from a planar multi-layer laminate is also provided. The front sheet and the rear sheet are sealed together along a portion of a common peripheral edge to define a volume enclosure. The front sheet and the rear sheets are heated in a first localized area to fuse them together along the heated first localized area and thereby form a first peelable seal. This first seal extends between a first side of the common peripheral edge and an opposing second side of the peripheral edge. The first seal separably joins the front sheet to the rear sheet and thereby forms a first compartment within the volume enclosure for containing a diluent. The front and rear sheets are also heated along a second localized area to form a second peelable seal. The second peelable seal extends between the first side and the opposing second side of the common peripheral edge and separably joins the front and rear sheets together to thereby form a second compartment for containing a medicament. The second compartment is disposed between the first compartment and the outlet compartment.

The method also includes providing a first sacrificial port interposed between the front and rear sheets and in communication with the first compartment. A second sacrificial port is also interposed between the front and rear sheets. However, the second sacrificial port is spaced apart from the first sacrificial port and is fluidly connected with the second compartment. An outlet port is also interposed between the front and rear sheets. The outlet port is fluidly connected with the outlet compartment. The portion of the volume enclosure forming the first compartment is then expanded to permanently stretch the front sheet and the rear sheet and to thereby increase the volume capacity of the first compartment.

BRIEF DESCRIPTION OF THE DRAWINGS

These and other features, aspects and advantages of the present invention will be more fully understood when considered with regard to the following detailed description, appended claims and accompanying drawings wherein;

FIG. 11 is a perspective view of an embodiment of a tool for permanently stretching the front and rear sheets of the flexible container according to the principles of the present invention;

FIG. 12 is a perspective view of an upper portion of the tool of FIG. 11, showing the upper cavity;

FIG. 13 is a perspective view of an embodiment of an actuator housing for use with the tool of FIG. 11;

FIG. 14 is a semi-schematic perspective view of a handling container provided in accordance with the principles of the present invention, including a rail cartridge and a sealable film lid;

FIG. 15 is a semi-schematic plan view of the rail cartridge of FIG. 14, showing a plurality of flexible containers loaded into the rails;

FIG. 16 is a semi-schematic side elevational view of the loaded rail cartridge of FIG. 15 showing how the flexible containers are held within the rails by the sacrificial ports.

DETAILED DESCRIPTION

Figure 1:
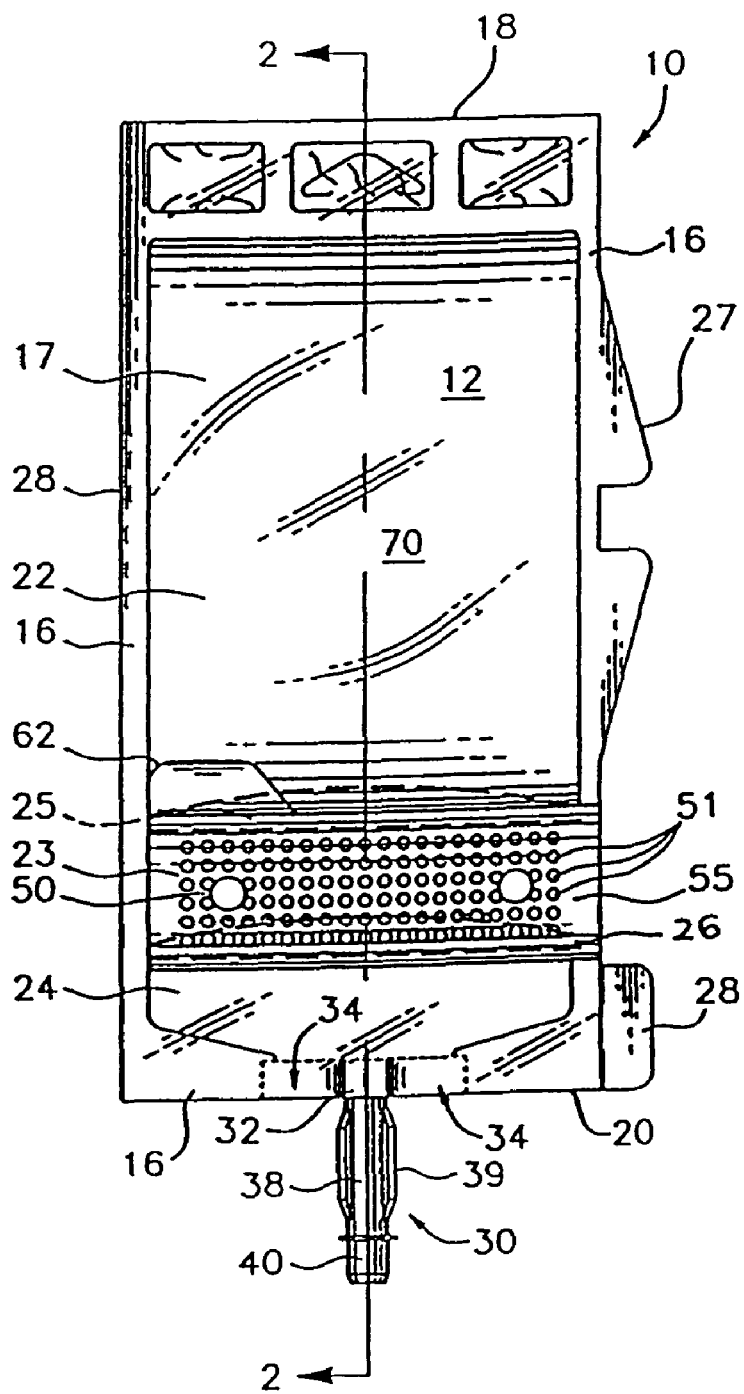
FIG. 1 is a semi-schematic front view of an exemplary embodiment of a container provided in accordance with the principles of the present invention.
Figure 2:
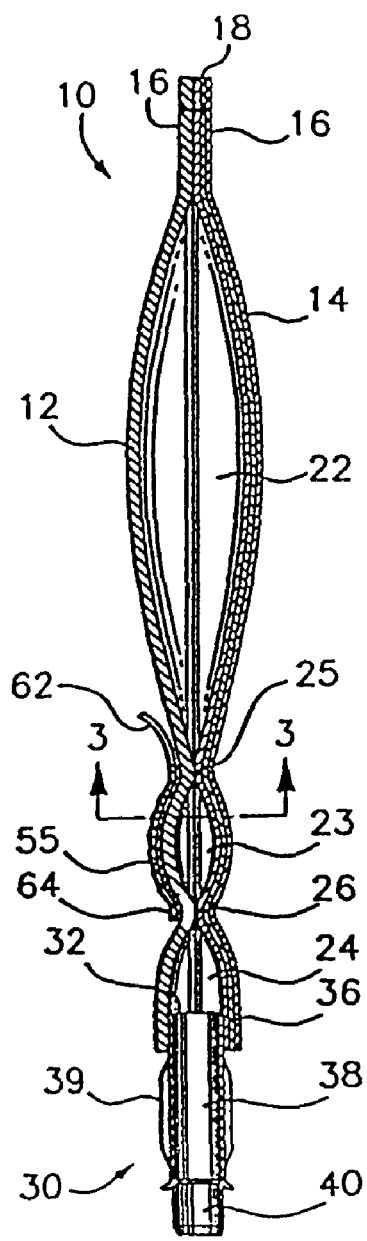
FIG. 2 is a semi-schematic side cross-sectional view taken along the line 2—2 of FIG. 1, depicting the flexible planar sheets formed in the container, with the thickness of the layers in the sheets exaggerated for clarity.

Referring to FIGS. 1 and 2, there is shown schematic front and cross-sectional side views, respectively, of a preferred embodiment of a flexible, sterile container 10 provided in accordance with practice of principles of the present invention. Although the container 10 can be viewed in any orientation, for purposes of explanation, the position of the compartments of the container relative to one another are described with reference to the orientation of FIGS. 1 and 2. The container 10 is formed from a generally planar front sheet 12 and an opposing generally planar back or rear sheet 14 (shown only in FIG. 2). The front and rear sheets 12 and 14 may be constructed of a single layer of flexible material or multi-layer laminates of flexible material which will be described in greater detail below.

The sheets 12 and 14 forming the container 10 may be provided separately and disposed opposing each other along a common plane 15 (FIG. 2). The sheets 12 and 14 are then sealed together along a common peripheral edge 16 with a permanent seal. Preferably, the sealed common peripheral edge 16 extends around the entire periphery of the container 10 to form a volume enclosure 17. Such peripheral seals may vary in configuration and width. A patterned seal, such as that depicted on the top or upper side 18 and the bottom or lower side 20 of FIG. 1, may be used to define grasping areas which allow clinical personnel to handle the container 10 and allow for the container to be attached to, for example, an IV support stand. Alternatively, the front and rear sheets 12 and 14 may be formed from a single film sheet which is subsequently folded-over and sealed together by means of the heat seal which extends around the periphery of the lapped-together portions of the film sheet. However formed, the sealed-together sheets shall be referred to herein as the "shell" or "body" of the container.

In the exemplary embodiment, the container 10 is partitioned into three separate compartments; a first or upper compartment 22, a second or intermediate compartment 23 and a lower or outlet compartment 24, each of which is sterile. The upper and intermediate compartments 22 and 23 are separated from one another by a first peelable seal 25, while the intermediate and lower compartments 23 and 24 are separated from one another by a second peelable seal 26. The peelable seals 25 and 26 extend between a first side 27 of the container 10 and an opposing second side 28. The peelable seals 25 and 26 span from the sealed common peripheral edge 16 on the first side 27 to the sealed common peripheral edge 16 on the second side 28. The peelable seals 25 and 26 join the interior faces of the front and rear sheets 12 and 14 together in the localized area or region of the seals.

A "peelable" seal, as the term is used herein, is a seal which is sufficiently durable to allow normal handling of the container yet which will peel-open, allowing separation of the front sheet from the back sheet in the region of the seal, under hydraulic pressure applied by manipulating the container, thereby allowing mixing and dispensing of the container contents. A peelable seal is formed by partially melting together the polymeric material present in the adjoining interior faces of the front and back sheets. The seal is obtained by a heat sealing process by which heat and pressure is applied to a localized area with varying times, temperatures, and pressures which will be described in greater detail below. Conversely, the seal along the common peripheral edge 16 is significantly stronger than the "peelable" seals 25 and 26 and will not be ruptured by the hydraulic pressures generated to separate the peelable seals. Each of the peelable seals, 25 and 26, are individually configured so as to peel-open in a manner that preferentially allows liquid medicament and liquid diluent to mix first, and then allow the mixed components to be dispensed.

In a typical application for the container 10 of the present invention, the upper compartment 22 is filled with a liquid diluent and the intermediate compartment 23 is filled with a medicament, typically provided in liquid form. The lower compartment 24 functions as a security interface for an outlet port 30 and remains empty until the container is used. The outlet port 30 extends downwardly and comprises a body portion 38 and a nozzle 40 which is configured for attachment to a standard IV administration device. A cap (not shown) is provided to cover the nozzle and maintain its sterility. The cap is removed just prior to attachment of an IV set to the outlet port 30. A plurality of ribs 39 may be provided in spaced-apart relationship about the body portion 38 of the outlet port 30 to provide an easily grasped surface and to facilitate attachment with an IV set.

The materials employed in constructing the front and rear sheets of the container 10 are selected based on the material to be stored therein. Preferably, at least one of the sheets is transparent to allow the contents of the container to be visually inspected and to allow the level of the solution in the container to be visually verified during dispensing. Suitable materials for the fabrication of the transparent sheet are typically single-layer and multi-layer laminated polymers and polymer films.

In particular, whether constructed of a single-layer or a multi-layer laminated polymer film, the materials comprising the front 12 and rear 14 sheets of the container 10 are chosen for their clarity and transparency. Conventional polyvinyl chloride (PVC) container materials are generally quite murky in appearance, making it difficult to adequately view the interior of the container and determine the levels of any fluids contained therein or the presence of particulate matter. This is a particularly dangerous situation when administering medication intravenously. It is imperative that a nurse or clinical worker be able to tell, at a glance, that any such medication being administered from a medical container is free from particulate matter.

Figure 3:
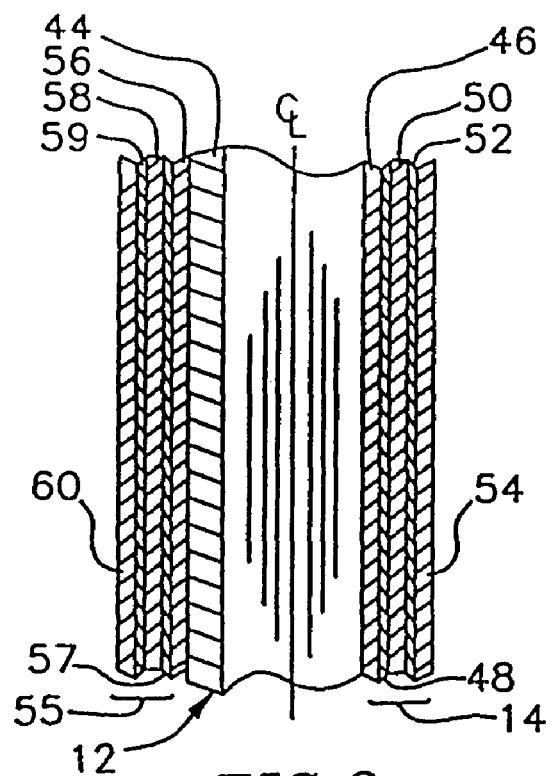
FIG. 3 is a semi-schematic fragmentary cross-sectional view taken along the line 3—3 of FIG. 2, showing the configuration of the flexible sheets of a first embodiment of the container of the present invention.

Referring now to FIG. 3, a fragmentary schematic cross-section of an embodiment of the container 10 is shown. As depicted, the front sheet 12 is constructed of a transparent, single-layer thermoplastic polymer film 44. The transparent film 44 may be fabricated from a planer layer or sheet comprising a blend of about 80% by weight polypropylene-polyethylene copolymer available from Fina Oil and Chemical Company of Deerpark, Tex., having a commercial designation of Z9450, and about 20% by weight styrene ethylene-butylene styrene thermoplastic elastomer, available from Shell Chemical Corporation under the trade name KRATON® and having a commercial designation G1652. G1652 thermoplastic elastomer is a two-phase polymer with polystyrene domains (end blocks) in a rubbery poly (ethylene-butylene) matrix and is typically provided in crumb form. In practice, the film is made by mixing pellets of the Z9450 co-polymer resin and G1652 thermoplastic elastomer, in crumb form, in an 80%/20% by weight ratio, in a high shear mixer and melting and repelletizing the mixture. Compounding the G1652 crumb in high shear equipment can cause the temperature to rise, so care should be taken so that the temperature is not allowed to exceed about 500° F. Subsequently, the transparent film 44 is formed from the blended pellets in a commercial extrusion apparatus.

The transparent polymer film 44 comprising the front sheet 12 may be constructed with varying thicknesses, depending on the use to which the container is put and the durability required for that particular application. Suitable thicknesses for the material comprising the front sheet 12 may range from about 3 to about 15 mils, but in the illustrated container embodiment, the transparent polymer film 44 comprising the front sheet 12 is preferably about 12 mils thick.

Although the composite material chosen for forming the transparent polymer film 44 (which may be referred alternatively as the "80:20 film") were chosen based on their clarity and transparency, the film 44 is also particularly suitable for forming both "peelable" seals and permanent seals, such as the permanent seal along the common peripheral edge 16 of the container 10. As will be described in greater detail below, the 80:20 film, in accordance with the invention, is able to accommodate both lower-temperature peelable seal and higher-temperature permanent seal formation processes without effecting the material's integrity or its ability to provide an effective peelable or permanent seal.

For certain medical solutions, including certain combinations of diluents and medicaments, the rear sheet 14 can be formed with the same single layer composition and configuration as the front sheet 12. Alternatively, multi-layer films, which include layers that are impermeable to moisture and light and are able thereby to extend the shelf life of a filled container, are preferred films for construction of the rear sheet. As illustrated, a three-layer laminate rear sheet 14 may be employed. Preferably, the laminate rear sheet 14 is a flexible planar sheet that is impermeable to water vapor and light. This configuration preserve the effectiveness and activity of the solution in the single compartment container 10 and the binary components (the unmixed medicament and diluent liquids) with multi-compartment containers and thus, increases the shelf life of the filled container.

In the exemplary embodiment illustrated, the rear sheet 14 includes an inner sealing or seal layer 46 on its inwardly facing surface. This inner seal layer 46 may be constructed of an 80%/20% wt/wt blend of polypropylene-polyethylene copolymer and styrene ethylene-butylene styrene thermoplastic elastomer the blend having a thickness of about 3 to 6 mils (the 80:20 film). Preferably, the inner seal layer 46 (the 80:20 film layer) may be approximately 6 mil. thick, which is bonded by means of a transparent inner adhesive 48 to an intermediate layer 50. Preferably, this intermediate layer 50 may be an approximately 0.7 mil to 1.3 mil, and more preferably about 1.0 mil, high-barrier aluminum foil layer. An outer layer 54 is provided on the outwardly facing surface of the rear sheet 14 and is bonded to the high-barrier aluminum foil layer 50 by means of a suitable transparent adhesive 52.

The inner adhesive layer 48 may comprise a modified aliphatic polyester polyurethane adhesive, available from Liofol Company of Cary, N.C., under the commercial designation TYCEL 7909. The outer adhesive layer 52 may comprise a modified aromatic polyester polyurethane adhesive, also available from Liofol Company of Cary, N.C., under the commercial designation TYCEL 7900. The aliphatic adhesive comprising the inner adhesive layer 48 may also be used for the outer adhesive layer 52, although the converse is not the case. The aromatic adhesive, while providing a stronger bond than the aliphatic version, has the potential for introducing extremely undesirable aromatic compounds into either the liquid diluent or liquid medicament, through the 80:20 film layer. Accordingly, the aromatic adhesive, when used, is only used when the aluminum foil layer 50 is interposed as a barrier between it and the volume container 17 within the container 10.

The aluminum foil layer 50 is suitably constructed of a commercially available 1.0 mil aluminum foil, such as ALCAN 1145, available from the Alcan Rolled Products Company, of Louisville, Ky. When the aluminum foil layer 50 remains exposed as the exterior layer of the rear sheet 14, the heat sealing process, used to form both the seal along the common peripheral edge 16 and the transverse peelable seals 25 and 26 may damage the foil layer 50 and degrade its integrity and ability to provide a barrier. The outer high temperature layer 54 is provided to prevent this damage. Preferably, the outer layer 54 is constructed of a relatively high-melting polymer which functions as a protective layer over the aluminum film and prevents contact between the intermediate foil layer 50 and the hot platens of a heat seal apparatus. Further, the high-temperature layer 54 functions as a heat seal release (also termed mold release) layer because the material does not melt and stick to the heat seal platens at the temperatures used during the seal formation processes. Pressure and temperature can thus be applied to the exterior of the container without the need for special coatings on the platens. Preferably, the outer layer 54 may have a higher melting temperature than the inner seal layer 46.

The outer high-temperature layer 54 is preferably a polyethylene terephthalate (designated herein as PET) available from Rhone-Poulanc under the commercial designation TERPHANE 10.21, having a thickness in the range of from about 0.4 to about 0.06 mils. In the illustrated embodiment, the thickness dimensions of the components of the multilayer laminate film 14 are preferably about 0.48 mils for the outer, high-temperature polyester layer 54, about 1.0 mils for the high-barrier aluminum foil layer 50, and about 6.0 mils for the 80:20 inner seal layer film 46.

It has been found that preferable material choices for the front and rear sheets 12 and 14, which result in optimum performance of the peelable seals 25 and 26, incorporate an interfacing seal layer on each sheet comprising the 80:20 film. Alternatively, the inner facing seal layers of the front and rear sheets may comprise polypropylene-polyethylene co-polymer and styrene ethylene-butylene styrene thermoplastic elastomer blends having differing relative percentages. The relative percentages used will depend on the characteristics of the various seals contemplated for use in connection with a particular medical container, and the temperature and pressure parameters of the seal formation processes. Other types of flexible films which may be useful in the construction of the front and rear sheets of the shell of the container 10 of the present invention, as well as the inner facing seal layers on both sheets, are disclosed in U.S. Pat. Nos. 4,803,102, 4,910,085, 5,176,634 and 5,462,526, the entire disclosures of which are expressly incorporated herein by reference.

In certain applications, particularly with multi-compartment containers, such as the container illustrated in FIGS. 1–2, additional protection may be desirable. This may be especially true where the medicament is susceptible to contamination by water vapor or degradation caused by radiation in the visible or UV portion of the spectrum and thus, requires additional protection over the portion of the front sheet 12 covering the intermediate (medicament) compartment 23. However, this additional protection may be provided over any number of compartments or even over the entire front sheet 12. The additional protection may be provided to preclude moisture, oxygen, and/or light transmission through the portion of the front sheet 12 comprising the second or intermediate compartment 23 and to protect the medicament from degradation. Such additional protection allows the container 10 to be stored for substantial periods of time without losing medicinal efficacy.

Referring in particular to FIGS. 2 and 3, an opaque film 55 having high-barrier properties, is employed to cover the intermediate compartment 23. The opaque film 55 interposes a barrier to moisture vapor and free oxygen permeation into the medicament compartment and, in the exemplary embodiment, comprises a multi-layer laminate structure which includes a high-barrier aluminum foil layer. The use of an opaque aluminum foil laminate helps prevent the medicament contained in the intermediate compartment 23 from being degraded due to exposure to invisible light and UV radiation. Thus, in the illustrated embodiment, the opaque aluminum foil comprising both a protective film 55 and the rear sheet 14 encloses the intermediate compartment 23 and prevents penetration of UV invisible spectrum light into the intermediate compartment 23 from either direction.

The high-barrier protective film 55 may be a multi-layer laminate, constructed of an inner seal layer 56 on its inwardly facing surface. In the exemplary embodiment, the seal layer 56 is a soft co-extrusion coated resin comprising a modified ethylenevinylacetate polymer available from the Dupont Chemical Company under the commercial designation APPEEL 1181, provided in a thickness of from about 0.2 to about 0.4 mils. An aluminum foil layer, such as ALCAN 1145, from about 0.7 to about 1.3, and preferably about 1.0, mils thickness is bonded to the inner seal layer 56 by means of a suitable transparent adhesive 57. An outer, heat seal release layer 60 comprising a polyethyleneterephthalate (PET) film, such as TERPHANE 10.21, approximately 0.48 mils in thickness, forms the outwardly facing surface of the high-barrier protective film 55. The heat seal release layer 60 is bonded over the aluminum foil layer 58 by means of a suitable transparent adhesive 59. The adhesive layers 57 and 59, of the present embodiment, suitably comprise a modified aliphatic polyester polyurethane adhesive available from Liofol Company under the commercial designation TYCEL 7909. Alternatively, the outer transparent adhesive 59 may comprise a modified aromatic polyester polyurethane adhesive, also available from Liofol Company, under the commercial designation TYCEL 7900. Because of the dangers attendant with aromatic compounds leaching into either the liquid diluent or liquid medicament, the aromatic adhesive is only used on the outside of the aluminum foil layer 58. The inner adhesive layer 57 will preferably comprise an aliphatic adhesive.

Because the inner seal layer 56 of the high-barrier protective film 55 may be a co-extrusion coated resin, it is able to form a peelable seal, over a broad temperature range, when applied to a number of different materials. Materials to which such a co-extrusion coated resin may form a peelable seal include acrylonitrile-butadiene-styrene (ABS), high density polyethylene (HDPE), high impact polystyrene (HIPS), polypropylene (PP), polystyrene (PS), polyvinylchloride (PVC), and the 80:20 film which comprises the front sheet 12 of the container. The high-barrier protective film 55 may thus be removably (peelably or separably) affixed to the outer surface of the front sheet 12 covering the intermediate or the medicament compartment 23.

Preferably, the high-barrier protective film 55 is removable (peelable or separable) from the container 10 prior to its use, to allow visual examination of the state of the medicament in the medicament compartment 23. In the exemplary embodiment, best seen in connection with FIG. 1, a protective film 55 includes an extending tab 62 which may be grasped in order to peel the protective film 55 away from the transparent front sheet 12. The contents of the medicament compartment 23 are thereby exposed for easy visual inspection.

The high-barrier protective film 55 may be sealed and adhered to only a portion of the front sheet 12. Preferably, those portions of the high-barrier protective film 55 which are not sealed to the underlying material of the front sheet 12 define a regular array or pattern of generally circular raised dimples 51 which are the tactile residue of a heat seal bar into which a rectangular array of holes has been cut. When the heat seal bar is pressed over the surface of the high-barrier protective film 55, a heat seal is provided only on the surface contact regions of the heat seal bar and not in the regions where the bar material has been removed (the holes). Since pressure is also applied during the process along with heat, the high-barrier protective film 55 takes a reverse impression from the heat seal head, thus giving rise to the textured, raised dimpled surface. The dimples 51 allow the high-barrier protective film 55 to be adequately sealed to the underlying material (the front sheet) of the medical container but, at the same time, provides for easy removal of the film 55 without application of undue force.

If the entire protective layer 55 was heat sealed onto the front sheet 12, a relatively strong bond would be created and a larger than desired amount of force would be required to completely peel it away. By reducing the adhered surface area of the seal, a smaller force (proportional to the seal area) is required to remove the peelable opaque barrier. It is apparent from the foregoing description, that the amount of force required to remove the peelable aluminum strip is inversely proportional to the number of dimples (51 of FIG. 1) formed in the film 55. Depending on the use to which the medical container is put, a more or less easily removable high-barrier protective layer may be easily constructed by merely increasing or decreasing the number of dimples formed in the layer during the heat seal process. It should be noted, however, that the high-barrier film 55 has its entire periphery, with the exception of the tab 62, heat-sealed to the underlying material of the container. Forming a full peripheral seal around the high-barrier film 55 ensures that the film's barrier properties fully extend across the medicament compartment 23.

In practical use, the filled container 10 may stored for a period of time against eventual need. Typically, prior to dispensing, a pharmacist or other user removes the high-barrier foil layer 55 from the front sheet 12 of the container 10 in order to visually check the integrity of the contents. If the container 10 is not put into use at that time, it is returned to storage and dispensed again at the next request. Removal of the peelable high-barrier film 55 leaves the contents of the container, or particularly, of the medicaments in the intermediate compartment 23 susceptible to degradation by moisture, light and permeable oxygen. It is desirable that filled containers 10 in accordance with the present invention are able to be stored for periods of up to 30 days prior to use without the medical solution or medicament being severely degraded by exposure to moisture and free oxygen after the high-barrier protective film has been removed from the medicament compartment.

Figure 4:
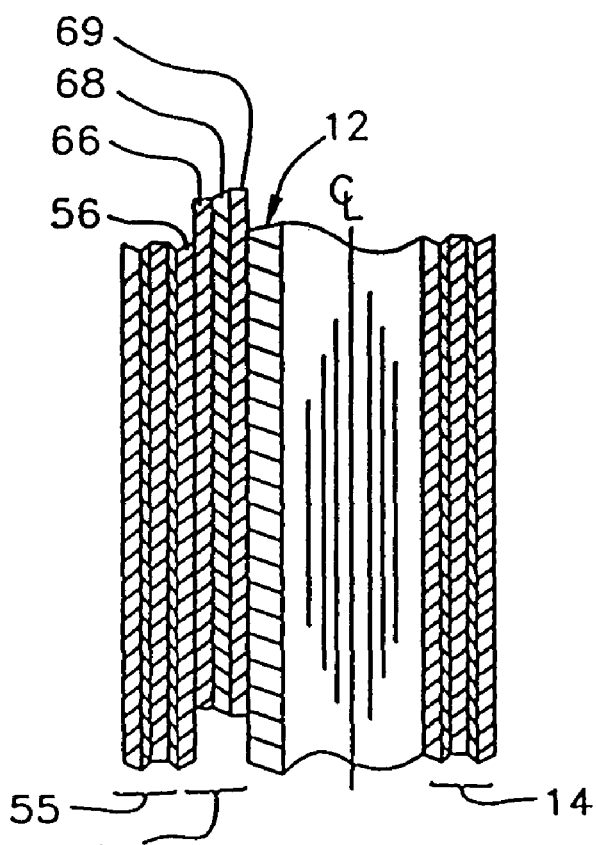
FIG. 4 is a semi-schematic fragmentary cross-sectional view of the configuration of the flexible sheets of a first embodiment of the invention depicting an optional, transparent, high-barrier intermediate film.

Accordingly, and as illustrated in FIG. 4, a transparent high-barrier intermediate laminate film 64 is optionally interposed between the high-barrier aluminum foil-containing protective film 55 and the 80:20 material of the container front sheet 12. Preferably, this intermediate laminate film 64 is disposed over the portion of the front sheet 12 covering the intermediate compartment 23. In this configuration, the transparent high-barrier intermediate film 64 covers and protects the contents of the intermediate compartment 23 after the peelable high-barrier protective film 55 is removed from the container 10. The transparent high-barrier intermediate film 64 exhibits barrier properties which protects medical solutions and medicaments from at least moisture vapor and oxygen permeation for a substantial period which, depending on the specific activity of the medicament, may be as long as 30 days. In other words, the opaque high-barrier protective film 55 in combination with the transparent high-barrier intermediate film 64 may be used to form a high-barrier protective covering over the intermediate compartment 23.

Pertinent to the characterization of the protective covering as a "high" barrier covering is the degree to which the protective covering is impermeable to various penetrant gasses. Polymers are categorized by the degree to which they restrict passage of penetrant gasses, e.g., oxygen or moisture vapor. The categories range from "high" barrier (low permeability) to "low" barrier (high permeability). The category in which a polymer is classified may vary according to the penetrant gas. As used herein, the term "high"-barrier, when it refers to moisture vapor permeability, means a film of a permeability of less than about 1.5 $g/mil/m^2/24$ hr/atm, at 30° C., 100% R.H. As used herein, the term "high"-barrier when it refers to oxygen permeability, means a film with a permeability of less than about 50 $cc/mil/m^2/24$ hr/atm, at 25° C., 100% R.H.

The transparent high-barrier intermediate film 64 may include a triple layer high-barrier laminate structure which is significantly resistant to free oxygen and water vapor permeability so as to protect the contents of the medicament compartment and increase the shelf life of a binary container. In the illustrated embodiment, the intermediate laminate film layer 64 includes an outer layer 66 of silica deposited polyethyleneterephthalate (also termed $SiO_x$ coated polyester or $SiO_x$ coated PET) available from Mitsubishi Kasei under the commercial designation TECH BARRIER H. The sealant layer 56 of the high-barrier protective film 55 is placed in contact with the outer layer 66 of the intermediate laminate film 64. An intermediate layer 68 comprising a silica deposited ($SiO_x$ coated) polyvinylalcohol (PVA) film available from Mitsubishi Kasei under the commercial designation TECH BARRIER S is bonded to the outer layer 66. On its inward facing surface, the transparent high-barrier intermediate film 64 suitably comprises an inner seal layer 69 formed of a polypropylene-polyethylene copolymer. The copolymer may be blended with styrene ethylene-butylene styrene thermoplastic elastomer in various proportions, but a 100% polypropylene-polyethylene copolymer layer is preferred. The individual layers of the intermediate laminate film 64 are adhesively bonded to one another. For clarity, these adhesive layers are not shown in the figure but comprise a modified aliphatic polyester polyurethane laminate available from Liofol Company under the commercial designation TYCEL 7909. The inner seal layer 69 is securely affixed to the outer surface of the front sheet 12 by an appropriate permanent heat or ultrasonic seal, an adhesive pressure seal, or the like. The transparent high-barrier intermediate laminate film 64 is sized, horizontally and vertically, to cover the entire surface area of the medicament compartment and also extends to cover the peelable and permanent seals formed adjacent the medicament compartment.

Similar to the flexible, thermoplastic materials which comprise the front sheet 12, the three-layer laminate structure of the intermediate layer 64 is substantially optically clear and transparent to allow inspection of the contents of the medicament compartment 23. Thus, unlike polyvinyl chloride (PVC), and other similar materials, which are fairly hazy (translucent), the intermediate layer 64 of the present invention is visually transparent while imparting considerable protection against moisture and free oxygen degradation.

In particular, the barrier properties of the transparent, high-barrier intermediate laminate film 64 are substantially greater than those of conventional films, such as low-density polyethylene (LDPE), medium-density polyethylene (MDPE), linear low-density polyethylene (LLDPE), ethylene-vinylacetate copolymers (EVA), or blends of these polymers, in areas important to the functioning of the container, e.g., moisture and oxygen permeability. The oxygen permeability of the intermediate layer 64 is approximately 10 $cc/mil/m^2/24$ hr/atm. Conversely, the oxygen permeability of EVA copolymers, LDPE and MDPE, respectively, are approximately 2500 (EVA 5%), 8300 (LDPE), and 8500 (MDPE) $cc/mil/m^2/24$ hr/atm. The oxygen permeability of LLDPE is approximately the same or slightly higher than LDPE. Thus, the oxygen permeability of the transparent high-barrier intermediate layer 64 is orders of magnitude less than the oxygen permeability of polymers typically used to construct binary medical containers. In other words, the barrier properties of the high-barrier intermediate layer 64 are improved by several orders of magnitude over the barrier properties of polymers typically used to construct these containers.

Because of the intermediate laminate film's barrier properties, the peelable aluminum foil-containing protective film 55 may be removed by a pharmacist in order to perform visual inspection of the container's contents prior to dispensing, and the container may then be stored for a reasonable additional period of time without the danger of oxygen or moisture induced medicament degradation. Once the protective foil layer is removed, it is desirable that the container have a storage shelf life of about 30 days. After removal of the aluminum foil layer, the precise shelf life of the container which includes the clear high-barrier laminate film 64 depends necessarily on the moisture or oxygen sensitivity of the drug contained in the intermediate compartment 23. Drugs with a relatively low moisture sensitivity are able to retain efficacy for periods substantially longer than 30 days by virtue of being protected by the clear high-barrier laminate film 64. In addition, drugs with an extreme moisture sensitivity, i.e., those, that would normally begin to lose effectiveness upon exposure to water vapor upon removal of the aluminum foil layer, may be stored for periods up to two weeks without losing effectiveness because of the moisture barrier properties of the clear high-barrier film overlying the intermediate compartment 23.

Although the intermediate film 64 has been described in the exemplary embodiment as being affixed to the outer surface of the medicament compartment, it will be apparent to one skilled in the art that the intermediate layer may be sized to cover both the intermediate and the first compartments if desired. The intermediate film 64 may also be used to cover the entire front sheet 12. The manner of attachment of the intermediate layer 64 to the outer surface of the container may also be varied without departing from the spirit or scope of the invention. The intermediate layer 64 may be permanently secured to the outer surface of the container by a suitable adhesive, as well as by permanent heat or ultrasonic sealing. Alternatively, the intermediate film 64 may be removably provided on the surface of the container by adjusting the temperature and pressure characteristics of a heat seal in order to make the seal peelable. In this case, the film 64 could be peeled from the container 10 as is the case with the opaque high-barrier laminate film 55.

It should be noted that in the exemplary embodiment, the medicament is described as being in the form of a liquid. The medicament may also be in the form of a colloid, crystalloid, liquid concentrate, emulsion, or the like. In addition, the medicament may be provided as a dry powder such as antibiotic compositions or antiemetic compositions, with non-limiting examples of such being; cefizolin, cefuroxime, cefotaxime, cefoxitin, ampicillin, nafcillin, erythromycin, ceftriaxone, metoclopramide and ticar/clav. The intermediate compartment 23 need not be filled with a drug, per se. Other medical compositions such as lyophilized blood fractions, blood factor VIII, factor IX, prothrombin complex, and the like, are particularly suitable for dispensing from a container in accordance with the invention. While the container of the present invention has been described with multiple compartments and particularly, with a single medicament and diluent compartment, single compartment containers may be provided in accordance with the present invention as will be described in further detail below. In addition, containers which have multiple compartments filled with different diluents and/or different medicaments, may also be provided in accordance with the present invention.

While preferred materials for the clear, high-barrier intermediate film 64 would include both an oxygen barrier layer and a moisture barrier layer, alternate materials may be used to provide a medicament compartment cover which is adaptable for various particular uses. For example, one of the high-barrier layers may be omitted giving a high-barrier intermediate film which includes only a moisture barrier layer or only an oxygen barrier layer. Moreover, the high-barrier intermediate film 64 may include a moisture barrier layer, as described above, in combination with a heat sealed release layer which is constructed from a high melting temperature material which also exhibits some oxygen barrier properties.

Preferably, the flexible container 10 may be manufactured to a particular overall size or to a few sizes. This limits the need for duplicate machines or alternatively multiple machine set-ups and runs. As previously discussed, a single overall container size, such as the rectangular dimensions about the common peripheral edge 16, facilitates the handling of the container as well as the administering of the contained medical solutions. In particular, this allows fabrication, handling, sterilizing and marking of the containers 10 to be carried out with similar or identical machines and procedures and eliminates the need for multiple tooling and machine runs. However, restricting the overall size of the container 10 limits the volume of medical solution each compartment can hold.

In order to increase the capacity of the container 10, and in accordance with the principles of the present invention, at least one of the front sheet 12 and the rear sheet 14 is elongated or otherwise permanently stretched. Enlarging the volume capacity of the container 10 allows the fabrication of a single container design for storing and administering a much wider variety and combination of medical solutions and medicines. Since the enlarged containers are unchanged from the conventionally sized containers, there is no need to tool up to manufacture these specially sized bags. This is especially advantageous where smaller quantities of containers may be needed which may otherwise not be manufactured due to costs.

Figure 5:
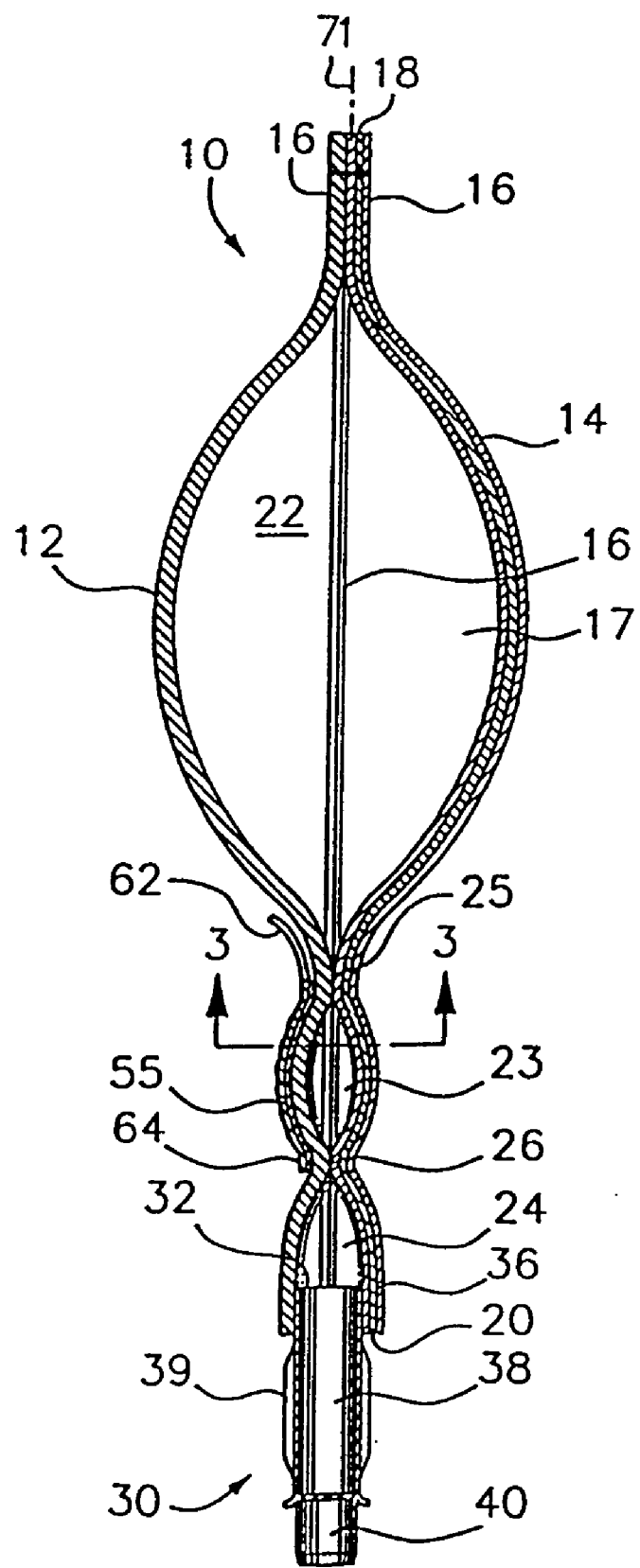
FIG. 5 is a semi-schematic side cross-sectional view taken along the line 2—2 of FIG. 1, depicting a permanently enlarged first compartment relative to FIG. 2.

Referring now to FIG. 5, a conventional or standard sized container 10 is shown with each of the front sheet 12 and the rear sheet 14 permanently stretched to increase the capacity of the first compartment 22. More particularly, the front sheet 12 and the rear sheet 14, each include a respective surface area 70. These respective surface areas 70 oppose each other across a common plane 71 which is generally defined along the common peripheral edge 16. The front sheet 12 and the rear sheet 14 have been enlarged through a permanent stretching of the respective surface areas 70.

In the embodiment illustrated, only the first compartment 22 has been enlarged. This configuration may be particularly useful when a greater than standard quantity of diluent is desired for use with a standard quantity of medicament. The front sheet 12 is stretched more or further elongated relative to the rear sheet 14. This is particularly true where the rear sheet 14 includes an aluminum or otherwise less expandable layer.

Manufacture and Assembly of the Container

Figure 6:
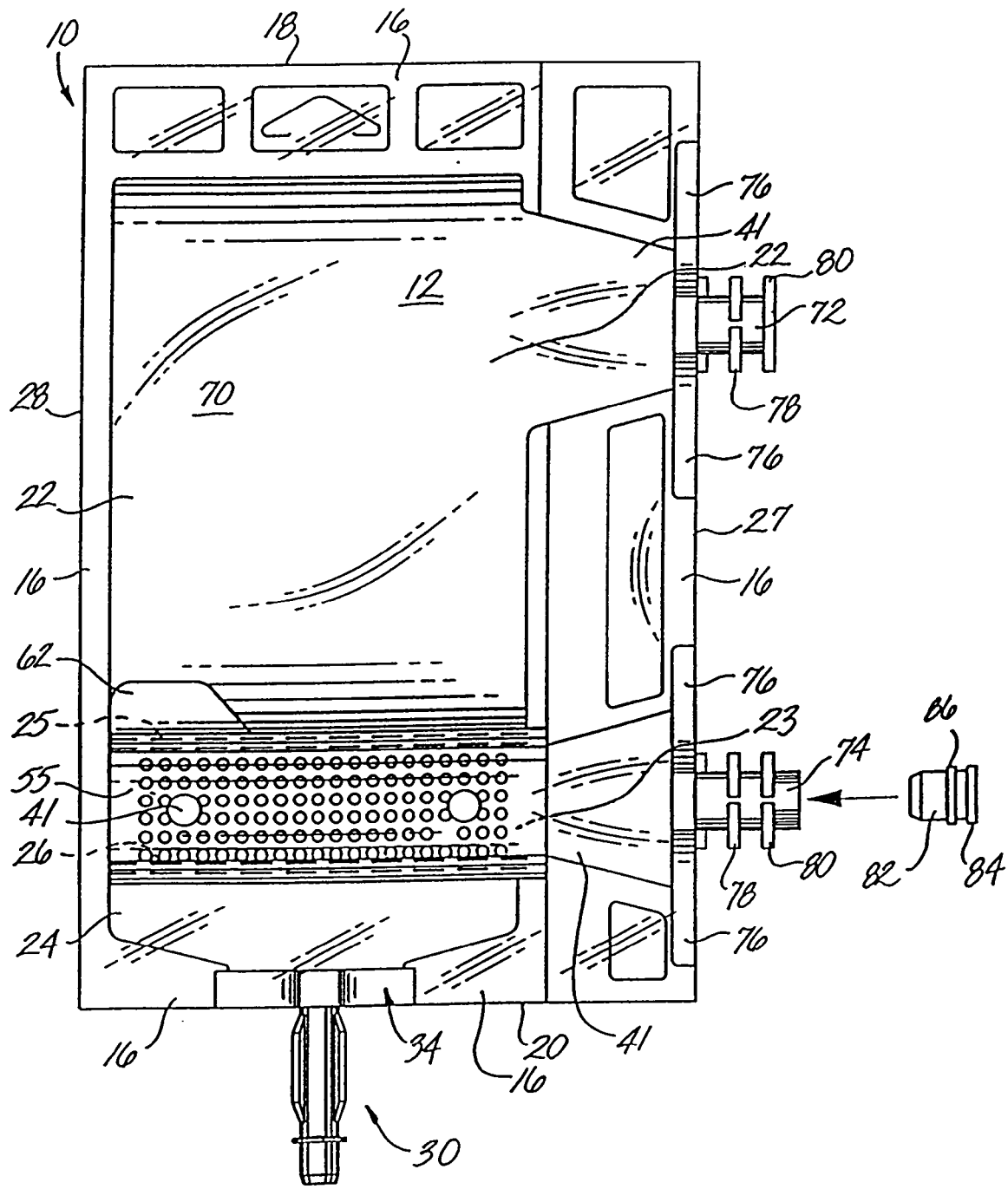
FIG. 6 is a semi-schematic front view of an exemplary embodiment of the container shown during fabrication in accordance with the principles of the present invention.

Referring now to FIG. 6, a method of manufacture and assembly of the flexible container 10 will be described in accordance with practice of principles of the invention. The front sheet 12 and the rear sheet 14 are disposed opposing one another. The inward facing layer of the front sheet 12 comprises an 80:20 film, which is placed in contact with the inward facing 80:20 film layer of the rear sheet 14. Other interfacing films may be used and are within the scope and contemplation of the present invention.

The composition of the front and rear sheets 12 and 14 of the container 10, allow for the creation of the seal along the common peripheral edge 16 and the peelable seals 25 and 26 using heat sealing techniques. Hot bars or dies are used at differing temperatures, pressures and application times to bring interfacing portions of the materials and laminates employed to temperatures near or above their melting points to allow migration of material across the interface to thereby form a bond of the desired strength and characteristics.

For either a single layer film, or a multi-layer laminate film, comprising the front sheet 12 and the aluminum foil laminate comprising the rear sheet 14, a procedure for fabrication of the container 10 is described. The procedure comprises cutting the front and rear sheets of the container to the desired vertical container dimensions, but oversized in the horizontal dimension.

If the container 10 is being constructed with a single layer front sheet 12, the high-barrier aluminum foil-containing protective layer 55 (of FIG. 3) and the transparent high-barrier intermediate layer (64 of FIG. 4), comprising the high-barrier covers for the second compartment 23 are cut to size, positioned over the area which will become the intermediate or medicament compartment, and sequentially attached to the container's front sheet 12. In accordance with the invention, the transparent high-barrier intermediate layer 64 is first laminated over the surface of the front sheet 12 followed by the aluminum foil-containing protective layer 55.

Specifically, the transparent high-barrier intermediate layer 64 is positioned over the second compartment 23 and held in place by a pair of rods or similar devices while it is being laminated onto the surface of the front sheet 12. The portion of the layer 64 in contact with the rods is, thus, not accessible to, for example, the heat seal head, resulting in a small portion of the film not being sealed onto the surface of the front sheet. The residue of the use of rods to secure the transparent high-barrier intermediate layer in position is a non-sealed area having the contact footprint of the rod. The rod contact surface is generally circular and results in two circular non-sealed regions 41 which remain visible because of the reverse imprinting caused by pressure applied during the sealing process. Following lamination of the intermediate layer 64, the aluminum foil layer 55 is applied over the surface thereof, using a patterned heat sealing die as described above.

After attachment of the aluminum foil layer 55 and the transparent high-barrier layer, the front and rear sheets 12 and 14 may be mated together and permanently sealed together along the common peripheral edge 16. The outlet port 30 may include a flange 34 which is inserted in its desired final position between the front and rear sheets 12 and 14 and fluidly connected with the outlet compartment 24. The outlet port 30 may be injection molded and may have a composition of 40% FINA Z9450 polyethylene-polypropylene co-polymer and 60% Shell KRATON G1652 styrene ethylene-butylene styrene thermoplastic elastomer. Following insertion of the outlet port 30 along the common peripheral edge 16, a heated die is employed to create a permanent seal between the outlet port flanges 34 and the bottom side 20 of the front and rear sheets 12 and 14 adjacent the flange 34.

The peelable seals 25 and 26, and any additional peelable seal, dividing the compartments and the container 10 are then created using, for example, double hot bars comprising a front bar in alignment with a rear bar constraining the front and rear sheets 12 and 14 therebetween to form the seals 25 and 26. For example, the front bar may contact the previously combined high-barrier protective film 55, intermediate films 64, and front sheet 12. This front bar is maintained at a temperature in the range of about 245° F. to about 265° F. The rear bar, which contacts the rear sheet 14, is maintained at substantially the same temperature as the front bar (in the range of about 245° F. to about 265° F.) and may optionally include a thin rubber coating to assure uniform application of pressure. The double bars are pressed into contact with the front and rear sheets with a pressure in the range of from about 230 psi to about 340 psi and maintained at that temperature and pressure for a period of time between about 1.5 to about 2.5 seconds. The peelable seals 25 and 26 may also be made individually with a single double bar set up, or simultaneously with a twin double bar set up. Any additional peelable seals may be easily accommodated by a triple double bar set up.

Following the formation of the peelable seals 25 and 26, the front and rear sheets 12 and 14 are mated together and sealed by a peripheral permanent heat seal which extends along the common peripheral edge 16. This permanent seal is spaced-away from the oversized edge of the first side 27 of the container and provides openings between the front and rear sheets 12 and 14.

In other words, the permanent seal is continuous along the vertical upper side 18, the second side 28 and the vertical bottom side 20 and broken along the first side 27 to allow access to the first and second compartments 22 and 23. The permanent seal does not affect the fluid connection of the outlet port 30 with the outlet compartment 24.

A first sacrificial port 72 may be inserted between the front and rear sheets 12 and 14 and fluidly connected with the first compartment 22. In a similar configuration, a second sacrificial port 74 may be inserted between the front and rear sheets 12 and 14 and fluidly connected with the second compartment 22. Preferably, each of the sacrificial ports 72 are positioned and supported along the common peripheral edge 16 of the first side 27 within the gaps in the permanent heat seal. The sacrificial ports may be supported by the common peripheral edge 16 in a similar configuration to the outlet port 30. Thus, each of the sacrificial port 72 and 74 includes tapered mounting flanges 76 which are interposed and sealed between the front and rear sheets 12 and 14 along the common peripheral edge 16 of the first side 27. The sacrificial ports 72 and 74 may be injection molded. Preferably, the sacrificial ports 72 and 74 are constructed from an inexpensive thermoplastic material, since they will be removed and disposed of at a later stage in the process. In particular, the sacrificial ports 72 and 74 may be constructed of 80:20 film "regrind" material, simple polypropylene, or any other similar material.

The sacrificial ports 72 and 74 are an important feature of the present invention and provide a means for aseptically filling a single compartment container with a medical solution or a multiple compartment container with a liquid diluent in the first compartment 22 and a medicament or similar in the second compartment 23. In addition, the sacrificial ports 72 and 74 are provided with structure to allow the ports and, thereby, the flexible medical container 10 to be supported and manipulated by automated robotic machinery.

As depicted, each sacrificial port 72 and 74 includes a lower flange 78 and a spaced apart upper flange 80. Each of the flanges 78 and 80 may be generally rectangular or otherwise shaped to facilitate handling. Particularly, each of the flanges 78 and 80 may be particularly configured for operation with support and handling equipment. An inner bore through each of the sacrificial ports 72 and 74 provides communication with each of the respective compartments 22 and 23.

A generally cylindrical cap or plug 82 is provided for each of the sacrificial ports 72 and 74. The caps 82 may be constructed having an outer diameter which is slightly larger than the inner bore of each of the sacrificial ports 72 and 74, such that when the cap 82 is inserted, the interface between the cap outer diameter and the port inner diameter provides a hermetic seal. This frictional seal is required to prevent particulates from entering the container 10 prior to filling and for preventing powdered medicaments or liquid diluents from escaping after the container has been aseptically filled. Preferably, each of the caps 82 may have a beveled bottom edge, so as to engage a similar chamfer on each of the respective sacrificial ports 72 and 74.

In addition to the flanges 78 and 80 on the ports, a pair of vertically spaced-apart flanges are also provided on the cap 82. In the exemplary embodiment illustrated, a generally circumferential upper flange 84 defines the top of the cap 82. The upper flange allows a "lifting" mechanism to engage the underside of the upper flange 110 and provide a means to lift the cap vertically out of its respective port barrel 72 and 74. A lower flange 86 may also be provided about the cap 82. The lower flange 86 limits the penetration depth of the cap 82 during insertion into the port barrel 72 and 74 or when reseated after a filling operation. The lower flange 86 may be fully circumferential or, alternatively may be implemented as a partial flange defining a simple lateral extension from the body of the cap 82. The upper and lower flanges 84 and 86 are spaced-apart from one another, along the body of the cap 82.

These manufacturing steps form the described flexible container 10 having a conventional configuration with non enlarged compartments 22 and 23. As previously discussed, the first compartment 22 may be enlarged to increase the available storage volume for diluent. In a similar fashion, the second and the outlet compartments 23 and 24 may also be enlarged. This may include permanently stretching at least one of the front sheet 12 or the rear sheet 14 by inflating the respective compartment 22, 23 and 24 with a pressurized gas as will be described in greater detail below.

Container Fabrication Apparatus

In accordance with practice of principles of the present invention, a procedure and apparatus for fabricating the container 10 of FIG. 6, will now be described in connection with FIG. 7. As will be evident from the following description of a container fabrication apparatus, both the apparatus and procedure are adapted to be suitable for manufacturing medical containers with front and rear sheets comprising either single layer or multi-layer laminate films. In addition, it will be evident from the following description that the number, shape, configuration and location of the various seals of the container 10 of FIG. 6, can be easily changed, or indeed even omitted, due to the modular arrangement of components of the apparatus.

Figure 7:
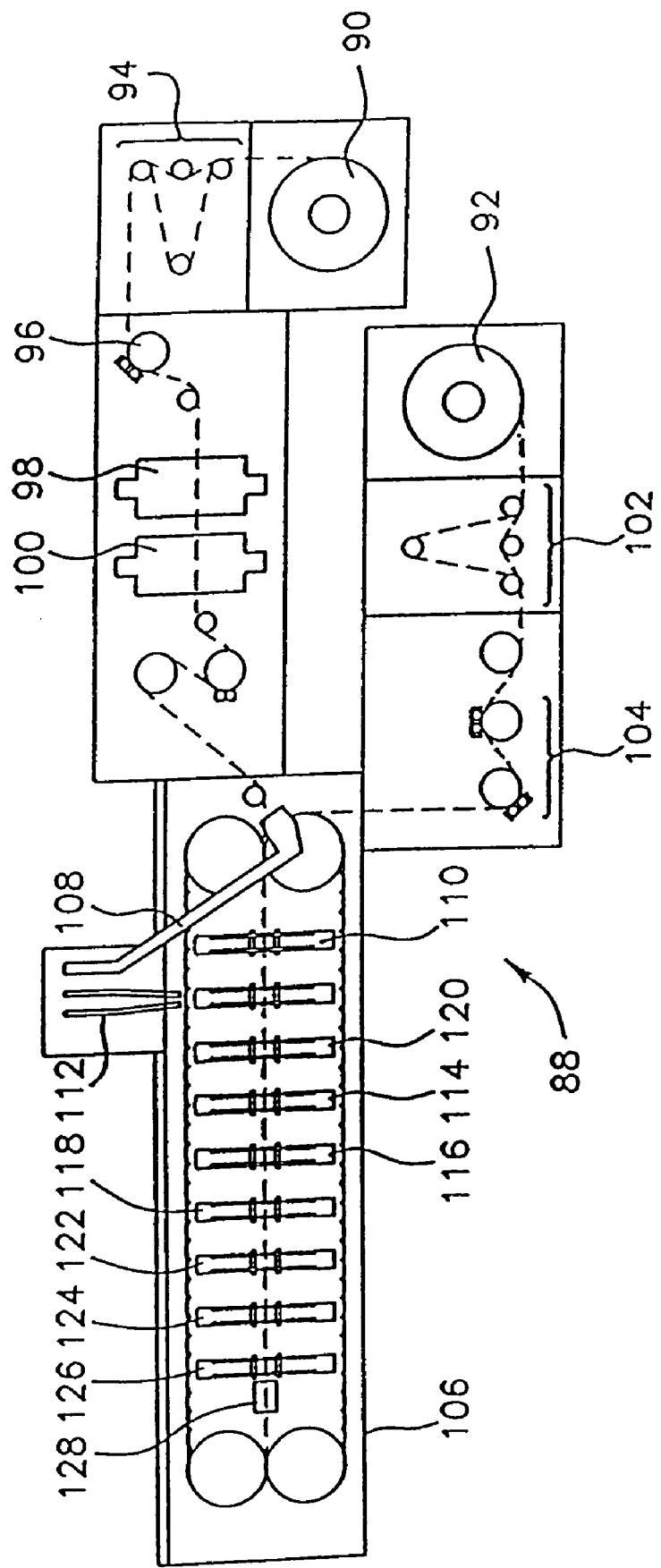
FIG. 7 is a diagrammatic plan view of an embodiment of a modular container fabrication apparatus in accordance with the present invention.

FIG. 7 is a semi-schematic plan view of an exemplary embodiment of a container fabrication machine 88 provided in accordance with the present invention, showing the arrangement and positioning of various seal forming stations and the arrangement and configuration of the container, primarily film web supply rolls.

Bulk material for the container front and rear sheets (12 and 14 of FIG. 2, for example) is provided to the container fabrication machine 88 in the form of respective bulk film web supply rolls 90 and 92, which are mounted at web supply roll stations at the intake end of the container fabrication machine 88. Web material from the, for example, front sheet supply roll 90 is threaded through a dancer station 94 which functions to maintain the web material at a proper tension as the web is drawn through the remaining stations of the fabrication machine 88.

Following dancer station 94, the web material is transported by vacuum feed wheels past a first web cleaning station 96 and next through a series of optional barrier film application stations 98 and 100, disposed serially along the web path. If the container 10 is being constructed in the manner described previously, i.e., to include a single layer front sheet 12, a transparent high-barrier intermediate film (64 of FIG. 4) and a high-barrier aluminum foil-containing protective layer 55, the high-barrier covers for the second compartment 23 are first cut to size, next positioned over the portion of the surface area 70 which will become the second compartment, and then sequentially attached to the front sheet 12 of the container 10 in the barrier film application stations 98 and 100 respectively. In accordance with the invention, the transparent high-barrier intermediate layer is first laminated over the surface 70 of the front sheet 12 in application station 98 and the aluminum foil-containing protective layer 55 is overlaid thereto in application station 100.

In a similar manner, web material which will form the container rear sheet is threaded from its respective bulk web supply roll 92 through a corresponding dancer station 102, and is transported by vacuum feed wheels through a corresponding web cleaning station 104.

When the continuous films of front and rear sheet web materials 90 and 92 leave their respective preparation stages, they are fed into registration with one another and are oriented such that the 80:20 surfaces of each continuous planar film faces the 80:20 planar surface of the other film. Once the continuous film webs 90 and 92 have been put into registration, the web material is continuously indexed and longitudinally moved through the seal core 106 of the fabrication apparatus 88. Sacrificial first (diluent) and second (medicament) ports 72 and 74 are located along the web sandwich and positioned between the front and rear sheet film webs, and various seals are sequentially formed on the web sandwich material so as to join the webs together and substantially fabricate the container 10 into an intermediate stage suitable for expanding and aseptic filling, as best illustrated in FIG. 6.

In accordance with practice of principles of the invention, the fabrication machine seal core 106 comprises a multiplicity of seal presses and port insertion stations, arranged in series fashion along the travel path of the container film web sandwich. The first such station is a set port loading station 108, in which a set port, or outlet port 30 is inserted in its proper position between the front and rear sheets 12 and 14. A heated press, including a shaped die, is compressed over the web material to create a seal between the outlet port flange 34 and the eventual lower edge of the front and rear sheets adjacent the flange, at set port seal station 110.

The set, or outlet, port 30 is comprised of a plastic material and is injection molded from a composition of 40% FINA Z9450 polypropylene co-polymer and 60% Shell KRATON G1652 styrene ethylene-butylene styrene thermoplastic elastomer. Because of the similarities between the material composition of the set port 30 and the material of the inner, seal-forming surfaces of the front and rear sheet, it can be seen that the front and rear sheets may be sealed to the set port flange 34 using a substantially similar heat seal regime, as that used for the formation of the permanent, peripheral seals, to be described in greater detail below.

Following insertion and sealing of the set port 30 to the container material, the film web sandwich is next indexed to a sacrificial port insertion station 112, at which sacrificial ports (72 and 74 in FIG. 6) are inserted between the front and rear sheets, in positions along the first side of the container and connected with locations which will become the first and second compartments 22 and 23. The sacrificial ports 72 and 74 are preferably injection molded from a 100% polypropylene material but may also be fabricated of a material having a composition similar to the composition of the outlet port 30. In a manner likewise similar to the outlet port 30, the front and rear sheets are sealed to the sacrificial ports 72 and 74 along tapered flanges 76, which are provided for such purpose.

Following insertion of the sacrificial ports 72 and 74, the front and rear sheet film material is mated together by a permanent heat seal along a portion of the common peripheral edge 16 which extends across what will become the top 18, bottom 20, and one continuous side 28 of the finished container. Along the opposite side 27 of the container 10, the permanent heat seal is provided parallel to, but spaced-away from, the peripheral edge 16 of the film web sandwich strip, and is formed in broken-fashion along the desired edge of the finished container just inwardly from the common peripheral edge 16.

Following formation of the perimeter seal at the perimeter seal station 114, the container material is indexed to a first, optional, medicament sacrificial port seal station 116. The front and rear sheet material is sealed to the tapered flange 76 of the second sacrificial port 74 by compressing the front and rear sheet material to the tapered flange of the port by a pair of concave conformal heated sealing dies. As was the case with the set port die, the heated sealing die of the second or medicament seal station 116 is conformally shaped such that when the two halves of the sealing die are compressed together, they form a generally elliptical pocket having a shape which is the mirror image of the convex tapered sealing surface of the second sacrificial port.

Next, the web material is indexed to a second, optional, first compartment sacrificial port seal station 118, where the front and rear sheet material of the container is compressed and heat sealed to the tapered flange 76 of the first compartment sacrificial port 72.

It will be appreciated that the order of sealing the sacrificial ports to the container is purely arbitrary and that the second sacrificial port seal station 116 may just as easily follow the first sacrificial port seal station 118 as via versa. In addition, the seal stations for sealing the sacrificial ports 72 and 74 to the container 10 may precede perimeter seal station 114. In addition, a further optional seal station, peelable seal formation station 120 which is depicted in FIG. 7 as following the sacrificial port insertion station 110 and preceding the perimeter seal station 114, is optionally provided to form peelable seals between the first side 27 and the opposing second side 28 of the container 10. The peelable seals bisect and subdivide the container 10 into a plurality of compartments. Alternatively, the optional peelable seal station 120 may be configured to proceed the sacrificial port insertion station 112, by merely repositioning the peelable seal station along the film web path. It will be evident as well, that a multiplicity of peelable seal stations may be provided, if the container is to be fabricated with multiple compartments.

It should be evident to one having skill in the art, that the sequential, but independent, plurality of seal stations may each be configured to operate automatically as the film web is indexed to their respective stations. Alternatively, the seal stations may be present in the container fabrication machine, but rendered inactive, such that their particular seals are not formed on a specific production run. In particular, a container may be fabricated without any peelable seals as will be described in greater detail below. Following application of the sacrificial port seals, the container web material is indexed to a trim zone sealing station 122, which applies a permanent heat seal to the container material which contacts and overlaps some of the broken portions of the permanent seal along the common peripheral edge and extends to the edge of the container film material.

Following the heat seal process steps, the container may be indexed through a hanger punch station 124 or the like, which forms a hanger cutout of the top center of the container. Following stations 126 and 128 separate the containers by cutting the material web at the bottom end 20 (126) and then a top trim station 128 cuts away the container material at the top end 18, following which the container is unloaded from the fabrication machine 88 and container construction is substantially complete.

It will be evident to one having skill in the art that the number and configuration of compartments comprising the container is determined solely by the number and location of the various heat seals used to form the container. In addition, depending on the number of containers contemplated for the final product, a suitable number of sacrificial ports are provided and positioned along their respective material web edges. It will be understood that the modular manufacturing process according to the present invention is adaptable to manufacture medical containers having a single primary compartment, or multiple compartment containers having any number of compartments, by merely providing additional peelable seals and additional sacrificial ports with which to fill the compartments. For each configuration of compartments and sacrificial ports, the trim zone seal press at trim zone seal station 122 may be suitably reconfigured by removing one press face and substituting another, which is configured to provide one, three, four or the like channels or openings so as to connect a plurality of sacrificial ports to a plurality of compartments.

In similar fashion, it will be clear to one having skill in the art that the composition of the container front and rear sheets may be changed by suitably replacing the front and rear sheet film supply web rolls with other suitable materials. In particular, both the front and rear sheet supply rolls may be single layer 80:20 film such that the finished container is transparent on both sides. Because of the modular nature of the fabrication apparatus, the clear barrier application station and the foil barrier application station may both be rendered inoperable, as well as the peelable seal formation station, thus configuring the container fabrication machine to provide a single-compartment container which is completely transparent, and which may comprise a multiplicity of outlet ports, such as separate med ports and set ports.

Accordingly, the container fabrication machine in accordance with the present invention is seen as being suitable for manufacturing a wide variety of medical containers, having a wide variety of sizes, and a variety of seal configurations and port locations. All of the containers so manufactured will be seen to be suitable for expanding to enlarge their capacity and then for aseptic filling in accordance with the principles of the present invention as well as suitable for use in combination with a terminal sterilization procedure, if such is desired.

Seal Formation

The peelable seals 25 and 26 formed during the manufacturing process described above are straight-line seals which have a thin, rectangular shape. While they appear similar to conventional straight-line seals, the peelable seals of this embodiment are improved in that they exhibit a more predictable rupture characteristic across production lots, i.e., they exhibit a uniform resistance characteristic to manipulation pressure.

Without being bound by theory, it is thought that the peelability of the seals is attained by limiting the time, pressure and temperature to that necessary to fuse the interface between the inner layers of the front and rear sheets which have a lower melting temperature than the intermediate and outer layers of the rear sheet. The depth of the structural alteration in the inner layers in the fusion zone is limited, thereby imparting the peelable character to the seal while providing sufficient strength to prevent breakage in normal handling of the container. Preferably, the activation force for the container 10 of the present invention is tightly controlled to provide container integrity under extreme handling conditions, yet be easy to activate for all users. This activation effort or force is characterized by a burst pressure which is preferably approximately 4±1. pounds per square inch (psi). However, this pressure may be slightly increased to accommodate the larger volumes associated with the enlarged containers described herein.

In order to achieve such uniformity in the burst pressure of a generally rectangular seal, it has been determined that the critical parameter which must be controlled is temperature. Uniform burst pressure response is achievable by controlling the seal temperature to within ±2° F. Commercially available production heat seal apparatus are not able to control the variability in heat seal temperature to this desired range. However, the heat seal time is able to be controlled very precisely. Accordingly, time is chosen as the control parameter and adjusted to compensate for the variation in heat seal temperature. Time and pressure of the seal head are monitored to ensure that they are within acceptable ranges as described above and the heat seal time is adjusted accordingly. While the contact pressure is preferably in the range of from about 230 psi to about 340 psi, it will be recognized by one having skill in the art that the lower figure in the range (about 230 psi) is provided for convenience in setting the parameters of a production heat seal machine. So long as the pressure exerted by the heat seal bars on the container material is sufficient to force the material seal layers into contact over the surface area of the desired seal, a peelable seal will be formed given an appropriate temperature and time. Indeed, it has been experimentally determined that variations in heat seal temperature and time beyond those contemplated by the present invention result in seals that not only fail to exhibit the desired uniform resistance characteristic, but also fail to rupture completely along the length of the seal. Incomplete seal rupture often results in residual diluent, for example, remaining trapped in 90° corners where the peelable seals contact the permanent peripheral seals of the container. Accordingly, the diluent/medicament mixture ratio may not be as expected, and drug delivery may be at a higher concentration than desired.

Examples of specific time, temperature and pressure settings which will form peelable seals, in the 80:20 film of the illustrated embodiments, having a burst pressure of about 4±1 psi include: pressure 235 psi, temperature=257° F., and time=1.9 seconds; and pressure=235 p temperature=263° F., time=1.75 seconds.

Higher temperatures and associated pressures and times are used to provide the peripheral permanent heat seals and the outlet port seal, which produce structure altering effects in a greater proportion to, or depth of, the sealing layers. Such seals may be formed by heat sealing at a temperature of 290° F. and a pressure of up to 200 psi for about two seconds. Those skilled in the art will recognize that various techniques for forming both permanent and peelable seals may be used in the construction of the container of the present invention. In particular, it will be evident that controlling seal temperature to a greater degree (to within about ±2° F.) will also allow formation of peelable seals having uniform burst pressure. In addition, time is chosen as the control parameter for seal formation because it is able to be precisely controlled. Precision control of temperature, pressure, or both would give the same result.

Enlarging the Compartments

After the container 10 is brought to the stage of fabrication exemplified in FIG. 6, its volumetric capacity may be enlarged according to the principles of the present invention. In particular, any of the compartments 22, 23 and 24 may be expanded or otherwise enlarged to increase their volume capacity. For example, the first compartment 22 may be permanently expanded in order to increase the quantity of stored diluent. This may be particularly advantageous where a lower dosage of medicine is desired or where a more concentrated medicament is used.

The first compartment 22 may be expanded by stretching either the front sheet 12, the rear sheet 14, or both, outwardly from the common plane 70. This stretching elongates the film layers which comprise the respective front or rear sheet 12 and 14 in both the longitudinal and traverse directions. The compartments 22, 23 and 24 may be elongated or otherwise stretched in different amounts to accommodate varying increases in volumetric capacity.

For example, and as best illustrated in FIG. 5 in conjunction with FIG. 6, the first compartment 22 may be expanded by temporarily applying a supply of a pressurized gas to the first sacrificial port 72. The pressurized gas inflates the first compartment 22 and applies an expansion force over the surface area of each of the front and rear sheets 12 and 14. This force permanently stretches the materials of the front and rear sheets 12 and 14. Preferably, the first compartment 22 is permanently stretched or elongated in both the machine and transverse directions by the pressurized gas to the desired volume capacity. To facilitate the proper stretching and shape formation of each of the front and rear sheet 12 and 14, a tool or form having shaped cavities may be utilized as will be described in greater detail below. The pressurized gas may include compressed air. However other compressed gasses or even liquids may be used. Preferably the pressurization gas is 0.2 micron filtered air or nitrogen.

Figure 8:
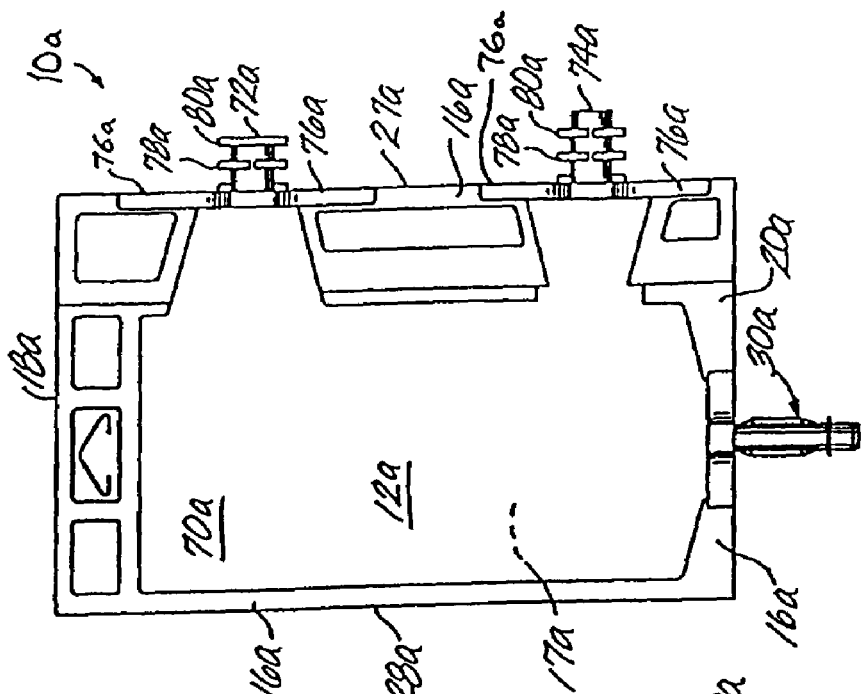
FIG. 8 is an alternative embodiment of a flexible container according to the principles of the present invention.
Figure 9:
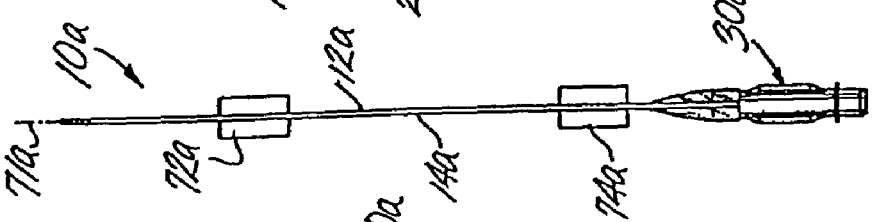
FIG. 9 is a side elevational view of the flexible container of FIG. 8.
Figure 10:
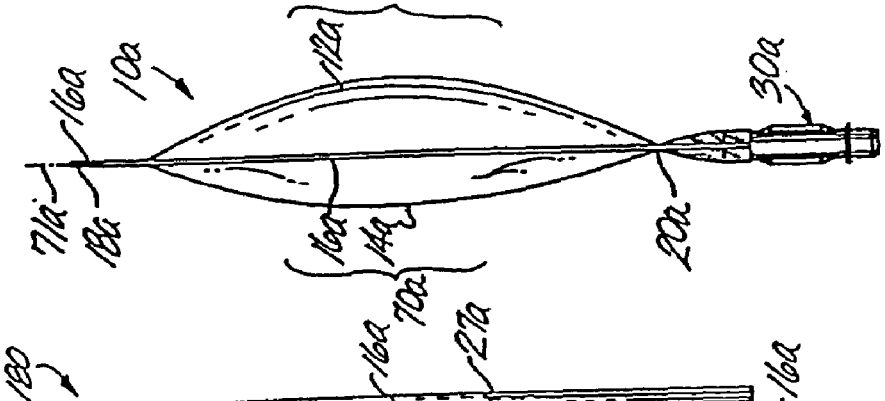
FIG. 10 is a side elevational view of the flexible container of FIG. 8 shown with the front and rear sheets permanently enlarged.

Referring now to FIGS. 8–10, an alternative, single compartment, embodiment of a flexible medical container constructed in accordance with the principles of the present invention is shown. In this embodiment, like features to those of the previous embodiment are designated by like reference numerals followed by the letter "a". As illustrated, a flexible container 10a may be provided for combined storage and administration of a medical solution.

In this embodiment, the front sheet 12a and the generally opposing rear sheet 14a are sealed together along a substantial portion of the common peripheral edge 16a to form a single volume enclosure 17a. If desired, the volume enclosure 17a may be divided into two or more separate compartments using peelable seals which extend from a first side 27a of the common peripheral edge 16a to an opposing second side 28a of the common peripheral edge 16a and separately join the front and rear sheets 12a and 14a together as previously described.

A pair of spaced apart sacrificial ports 72a and 74a may be supported along the first side 27a of the common peripheral edge 16 and an outlet port 30a may be supported along the bottom 20a. The ports 72a, 74a and 30a are positioned between the front and rear sheets 12a and 14a along the breaks in the permanent seal and heat sealed in place as previously described. The ports 72a, 74a and 30a are advantageously provided as part of this single compartment container 10a to facilitate the enlarging of the volume enclosure 17a as well as for use with common handling and fabrication equipment. Thus, the ports 72a, 74a and 30a and their fabrication may be identical to the previously described multi-compartment container.

The container 10a is fabricated to a standardized or non-expanded size. At this stage in the fabrication process, the container may be enlarged, or alternatively may retain its as-fabricated non-expanded volume enclosure and proceed to an aseptic filling step. In the example of FIG. 8, the container 10a may be fabricated having a substantially planar front sheet 12a constructed from a single polymer layer as previously described and a similarly sized opposing planar rear sheet 14a constructed from a multi-layer laminate as also previously described. The previously described transparent and opaque barrier layers have been omitted. Without a compartment for a medicament, these barriers are generally unnecessary. However, these barrier layers may be added or otherwise provided if, as will be described below, a multiple-compartment embodiment with an enlarged compartment or compartments, is desired.

The container 10a of FIG. 8 suitably comprises a length or vertical height along the first and second sides 27a and 28a of approximately 8.25 inches and a width across the top and bottom 18a and 20a of approximately 5.25 inches. In this embodiment, the permanent seal along the common peripheral edge 16a may define a volume enclosure 17a with maximum planar dimensions of approximately 7.0 inches by approximately 3.5 inches. These dimensions are approximate and do not account for open spaces between the sacrificial ports 72*a* and 74*a* and the volume enclosure 17*a*. The described container 10*a* thus, provides a surface area 70*a* of approximately 24.5 square inches for each of the front and rear sheets 12*a* and 14*a*.

As fabricated, the single compartment container 10*a* has a particular volume capacity of approximately 130 to 150 ml [milliliters]. For purposes of example only, this capacity is defined by simply filling the volume enclosure 17*a* with a fluid and then measuring that quantity in a graduated cylinder. However, a larger volume capacity may be desired within the general rectangular bounds of the described container. As discussed, the overall capacity of the container 10*a* may be greatly increased by stretching at least one of the front and rear sheets of the volume enclosure 17*a*. This may include stretching each of the sheets 12*a* and 14*a* a different amount. Preferably, the expanded front and rear sheets 12*a* and 14*a*, are each stretched outwardly or away from a common plane 71*a*, as best illustrated in FIG. 9, to each form a curved surface as best illustrated in FIG. 10. As used herein, the term planar, in relation to the front and rear sheets 12*a* and 14*a* refers to the respective sheets prior to being enlarged.

In some applications it might be desirable to stretch only one of the front and rear sheets 12*a* or 14*a*. In those cases the front sheet 12*a* is the most likely candidate for expansion. This is generally because the rear sheet 14*a* includes a layer of an aluminum foil or similar barrier layer and necessarily has a lower modulus of elasticity and generally, less responsive tensile properties. Since the front sheet 12*a* is a generally homogeneous layer with more responsive tensile properties, greater stretching is achieved when elongating the front sheet 12*a* over the rear sheet 14*a*. In addition, the rear sheet 14*a* is often used for markings, including administration and mixing instructions. Printing may be less effective on a stretched and curved sheet. Reading the printed information on a permanently stretched curved sheet may also prove difficult. However, in particular applications, the rear sheet 14*a* may also be solely stretched.

Pertinent to the elongation of either the front sheet or rear sheet 12*a* or 14*a*, the container fabricated in accordance with the present invention, is the recognition that the front and rear sheet's elongation characteristics depend on the particular materials from which they are fabricated. The physical tensile properties of the various single and multi-layer laminate films used in constructing a medical container relatively easily determined by the methods set forth in the ASTM D-882-81 specification. Typical tensile properties of various components of the single and multi-layer films described above are available from the film manufacturer via the particular film's technical data sheets. For example, KRATON G1652 styrene ethylene-butylene styrene elastomer has a typical tensile strength of about 4500 psi, exhibits an approximately 500% elongation at break, and has a modulus of about 700 psi at 300% extension. Similarly, Fina Z9450 copolymer has a typical tensile strength of about 2500 psi, while the aluminum foil layer (ALCAN 1145) has a typical tensile strength of approximately 9300 psi (0.001 gauge) and a typical elongation characteristic (at 0.001 gauge) of about 4.2%. It will be well understood by one having skill in the art that other films having different tensile strengths and different elongation characteristics will necessarily be expandable to a correspondingly greater or lesser degree than the films referred to above. Such differing elongation characteristics are easily calculable with recourse to ordinary test data taken at uniform jaw separation rates, uniform temperatures and uniform specimen shapes such as a dumbbell specimen cut with an ASTM die C.

Referring now to FIGS. 11–12, an embodiment of a tool or form 130 in accordance with the present invention will be described for use with enlarging the container 10*a* of the present invention. The tool 130 is configured for receiving at least a portion of the volume enclosure 17*a*. The tool 130 includes an upper tool portion 132 and an opposing lower tool portion 134. In the illustrated embodiment, the lower tool portion 134 has an internal cavity 136 and the upper tool portion 132 has an opposing internal cavity 138. A planar outer surface 140 surrounds each of the cavities with the exception for an opening 142 at one of the ports 72*a*, 74*a* and 30*a*. Other tool configurations may include a tool portion 132 or 134 which is not provided with a cavity, but has a substantially planar surface. This configuration is advantageous when only expanding one of the front and rear sheets 12*a* and 14*a*. Other configurations include altering the size and shape of each cavity 136 and 138 to conform the shape of the elongated front and rear sheets 12*a* and 14*a*.

The tool 130 may also include coupling devices 144, such as dowels and corresponding bores to ensure the upper and lower tool portions 132 and 134 remain stationary and interlocked during use. However, any other devices or methods may be used to retain the top portions 132 and 134 aligned and together. A sealing lip 146 may circumferentially surround at least one of the cavities 136 and 138 and follows the seal footprint of the compartment being expanded. The sealing lip 146 maintains the front sheet 12*a* and the rear sheet 14*a* together during the expansion process and retains the pressurized gas within its boundary. This prevents the inflation forces from being substantially transferred into the permanent seal along the common peripheral edge 16*a*. The sealing lip 146 may incorporate an o-ring or similar device and may be provided on each tool portion 132 and 134 or alternatively, on only one of the tool portions. The sealing lip 146 is preferably broken or otherwise interrupted around the opening 142. This allows the pressurized gas into and out of the volume enclosure 17*a*. Preferably, the opening 142 is located adjacent one of the ports 30*a*, 72*a* or 74*a* to allow inflation and deflation through that port.

In the embodiment illustrated in FIG. 11, the tool 130 is configured to receive the entire volume enclosure 17*a* of the single compartment container 10*a*. The container 10*a* is placed on the lower tool portion 134 with the outer surface of the front sheet 12*a* facing into the lower cavity 136 and the common peripheral edge 16*a* supported by the planar surface 140. The sealing boundary 146 is aligned just inside of the permanent seal along the common peripheral edge 16*a*. A pair of spaced apart sacrificial port slots 148 are disposed along a common side of each of the tool portions 132 and 134 and are each configured to receive one of the sacrificial ports 72*a* and 74*a*. An outlet port slot 150 is disposed along a second common side of the tool portions 132 and 134 and is configured to receive the outlet port 30*a*.

Once the container 10*a* is aligned within one of the tool portions 132 and 134, and preferably, the lower tool portion as described above, the opposing tool portions may be brought together. The upper tool portion 132 may be placed against the lower tool portion 134 and aligned such that the outer surface of the rear sheet 14*a* is facing the upper cavity 138 and the ports 30, 72*a* and 74*a* are received within the port slots 148 and 150. The planar surface 140 of the upper tool portion 132 is seated against the planar surface 140 of the lower tool portion 134 and restrainably sandwiches the entire common peripheral edge 16*a* with the exception of the opening 142. The opening 142 allows passage of the pressurized gas into and out of the first sacrificial port 72*a*. The sandwiched container 10*a*, may now be inflated with the pressurized gas to inflate the volume enclosure 17*a* and forcibly expand the front and rear sheets 12*a* and 14*a* against the cavities 136 and 138.

The tool 130 may also be provided in any other number of configurations as may be determined by those of skill in the art and thus, the exemplary embodiment is not meant to be limiting. Additional exemplary embodiments may include a tool having different sized upper and lower cavities or a tool with one tool portion having a cavity and the opposing tool surface being planar. This embodiment may be particularly useful where only one of the front and rear sheets 12*a* and 14*a* are to be stretched. Alternatively, the tool may have a number of differing cavities within each tool portion for use with multi-compartment containers. This embodiment may require an opening into each of the differing cavities for inflating the different compartments and planar surface sections on each of the tool portions for supporting the peelable seals defining each of the compartments. When enlarging only a single compartment of a multi-compartment container, each portion of the tool may include only a single cavity, but of a size just less than the compartments outer diameter, for example.

The sacrificial port slots 148 and the outlet port slot 150 may be configured to align the container 10*a* within the tool 130. Thus, they may include grooves for receiving the flanges 78*a* and 80*a* on the sacrificial ports 72*a* and 74*a* or have other configurations for fixably locating each of the ports. Alternatively, only one or two of the port slots 148 and 150 may be so configured. However, other devices and methods may also be used for aligning the container 10*a* within the tool 130 as is known to those of skill in the art. For example, alignment grooves may be provided along the planar surface 140 for receiving the at least a portion of the top, bottom or sides 18*a*, 20*a*, 27*a*, and 28*a* of the container 10*a*. Alternatively, a slot, notch or other alignment device (not shown) may be provided on the container 10*a* and a complementary alignment post or the like may be provided on the tool 130.

In a preferred embodiment, the tool 130, with the captured container 10*a*, is actuated on by an expansion machine 152 for inflation and enlargement, as best illustrated in FIG. 13. Preferably, the expansion machine 152 includes a table or operating base 154 for receiving and handling the tool 130. The tool 130 is then placed into a mouth 156 of the machine 152. Once inside the machine 152, cylinders 157 are used to clamp or otherwise maintain the opposing tool portions 132 and 134 together. The cylinders 157 can be hydraulic, electric motor driven, and the like, but are preferably pneumatic. Other devices and methods, such as pressure clips, may also be used to maintain the tool halves together during the expansion process.

A supply of a pressurized gas 158 is coupled to the opening 142 within the tool 130 and the container 10*a* is inflated with the pressurized gas 158 to fully expand the front sheet 12*a* into the lower cavity 136 and the rear sheet 14*a* into the upper cavity 138. This expansion permanently stretches and permanently elongates both the front sheet and the rear sheet 12*a* and 14*a* outwardly from the common plane as defined by the common peripheral edge 16*a* within the tool 130. The pressurized gas 158 may be maintained within the tool 130 for a brief period of time to maintain the front and rear sheets 12*a* and 14*a* against the respective cavities 136 and 138. Maintaining the volume enclosure 17*a* inflated reduces the amount of shrinkage or elastic rebounding. Typically, for the previously described film construction materials, this period is less than a minute. The pressurized gas 158 may then be relieved, the tool 130 removed from the expansion machine 152 and the enlarged container 10*a* removed from the tool 130. Preferably, this expansion operation is automated.

In the illustrated embodiment, the container 10*a* is expanded from an initial volume capacity or non-enlarged capacity of approximately 130 to 150 ml, to an enlarged volume capacity of approximately 250 to 300 ml as volume capacity is defined herein. Preferably, the container 10*a* is enlarged to a volume capacity of approximately 260 to 280 ml and more preferably to approximately 280±5 ml. To achieve these particular final dimensions on a single compartment container exemplified in FIG. 8, the upper and lower tool cavities 136 and 138 are configured to have a footprint area corresponding to the compartmental area of the container, i.e., approximately 7 inches by approximately 3.5 inches, and are each hollowed-out to a depth sufficient to define a volume of approximately 300 ml for the lower tool cavity 136 and a volume of approximately 100 ml for the upper tool cavity 138. Specifically, lower tool cavity 136 is hollowed-out to a depth of approximately 1.5 inches, while the upper tool cavity 138 is hollowed-out to a depth of approximately 0.6 inches. In addition, the sides of each of the cavities are blended into the cavity bottom with a continuous curvature so as to minimize any "hard corners" into which the container material might be forced, thereby distending the material.

Thus, the opposing tool cavities 136 and 138, when combined together, have a total volume of approximately 400 ml and a longitudinal cross-sectional area of approximately 24.5 square inches. These volumes and areas are not strictly precise, because the regions within the port slots 148 and 150 have necessarily not been taken into account. It should also be noted that due to the greater depth of the lower tool cavity 136 (and its consequent increased volume), the front sheet 12*a* will be allowed to stretch to a considerably greater degree than the rear sheet 14*a*. The reason for the difference in volume capacity between the upper and lower tool cavities is because the front and rear sheet materials are expanded until they contact the inner surfaces of the cavities. The depth of each cavity and its corresponding volume are configured to correspond to the typical tensile properties of the film which will be expanded into that cavity.

The volume enclosure 17*a* is preferably inflated with compressed air, having a pressure of between approximately 10 and 30 psi. for a period of approximately 1 to 30 seconds. Pressures of less than 10 psi may be used, however, the force developed is generally not sufficient to permanently stretch the described front and rear sheets 12*a* and 14*a* against the cavity. Utilization of differing materials, such as a container having two homogenous layers similar to the described single layer front sheet 12*a*, may allow effective stretching at 10 psi or lower. Pressures of approximately 30 psi and above tend to rapidly expand the front and rear sheets 12*a* and 14*a* against the cavities 136 and 138. This rapid expansion may stretch the material too fast which can lead to wrinkled material, delaminations within the laminate rear sheet 14*a* and other undesirable effects. It may be possible to utilize higher pressures by slowly or incrementally inflating the volume enclosure 17*a* in steps or alternatively, by heating the compressed gas. The sheet being expanded or the surfaces of the cavity may also be heated. These and other methods and devices may be used to modify the preferred pressures and times necessary to achieve the desired enlarged capacity for the container 10*a* as is known to those of skill in the art.

In a preferred embodiment, the volume enclosure 17a is inflated within the described tool 130 using compressed air regulated at a pressure between approximately 15 and 25 psi for between 15 and 25 seconds. More preferably, the pressure is regulated to approximately 20 psi and maintained for approximately 15 seconds at ambient temperature. Increasing the pressure or time can additionally stretch each of the films if the volumetric capacity of the expansion tool were correspondingly increased. This increased expansion would, of course, provide an increased volume in an expanded container. Likewise, decreasing the pressure or time results in reduced expansion and smaller volume capacities. These preferred parameters expand the front sheet 12a fully against the 300 ml lower cavity 136 and the rear sheet 14a fully against the 100 ml upper cavity 138 and result in an overall enlarged capacity of approximately 280 ml plus/minus 5 ml. Shrinkage due to the relaxation modulus in the materials results in the enlarged capacity of the container 10a being less than the combined volume of the cavities 136 and 138. In order to minimize further shrinkage, a deblocking process may be utilized as will be described in greater detail below.

The exemplary enlarging process described results in the surface area of the front sheet 12a being enlarged approximately 10% and the rear sheet 14a being enlarged approximately 6%. However, the preferred materials may be capable of being permanently deformed to much greater amounts, allowing for fabrication of containers having even greater volume capacities. For example, the surface area of the front sheet 12a, comprising the preferred 80:20 material, may be enlarged up to at least approximately 16% while the surface area of the rear sheet 14a, made from the preferred laminate material, may be enlarged up to approximately 10%. The surface area of the front sheet 12a, comprising the preferred 80:20 material, can be enlarged more than the surface area of the preferred rear sheet 14a due, in part, to the low elasticity of the aluminum layer in the laminate structure of the rear sheet.

Once the container 10a has been enlarged, it is deblocked. This process maintains a volume of a gas within the enlarged volume enclosure 17a sufficiently to maintain the enclosure in an expanded condition. Deblocking prevents the enlarged volume enclosure 17a from further shrinkage due to the inherent elasticity in the materials as defined by their relaxation modulus. This may be particularly advantageous for the front sheet 12a which is typically expanded to a greater elongation and is not supported by an adhered aluminum layer.

Deblocking includes inflating the container 10a with a low pressure gas to ensure the volume enclosure 17a is fully expanded to the enlarged configuration. The low pressure gas may comprise compressed air regulated to a few psi. However, other gases such as dry nitrogen may also be used. Preferably, the deblocking pressure is regulated to below approximately 10 psi, and more preferably to between about 1 to 5 psi. This prevents continued shrinkage, stress on the seals and the like. Once the volume enclosure 17a is fully expanded, the sacrificial ports 72a and the outlet port 30a are capped. Further shrinkage of the volume enclosure 17a will now meet resistance in the form of gas pressure within the sealed volume enclosure 17a. Deblocking may take place within the expansion machine 52. However, a deblocking station may preferably be provided.

An additional embodiment of a medical container fabricated with an expanded compartmental volume will now be described with reference to FIGS. 6, 11 and 12. FIG. 6 is a semi-schematic front view of a particular embodiment of a multiple-compartment container at the same stage in its fabrication process as the single compartment container illustrated in FIG. 8. The multiple-compartment container of FIG. 6 differs from the single compartment embodiment in that peelable seals 25 and 26 span the container and extend between the permanent peripheral seals 16 on either side of the container, to define an intermediate compartment 23 for containing a, for example, medicament. The peelable seals 25 and 26 also function to delineate a separate compartment 22 for containing a liquid diluent and an outlet compartment 24 which is initially empty. A multiple compartment container according to the embodiment of FIG. 6 and fabricated with the films and techniques described above, is capable of holding a relatively limited volume of diluent liquid in the diluent compartment 22. The multi-layer laminate rear sheet is a relatively stiff barrier material, as mentioned above, the stiffness of which limits the volume of diluent that can be introduced into the diluent compartment 22 to approximately 60 ml. Indeed, containers of the type illustrated in FIGS. 1 and 6 are commonly marketed as 50 ml containers, i.e., containing 50 ml of liquid diluent for mixing with a medicament prior to dispensation. The efficiency of various infusion therapies commonly require IV containers to be able to hold a substantially greater volume than the approximately 60 ml volume of the diluent compartment 22 of the container of FIGS. 1 and 6. Specifically, a PAB container manufactured and sold by McGaw, Inc. of Irvine, Calif. is commonly used to hold 100 ml of a 0.9% sodium chloride solution, in a condition termed partial fill. Thus, it can be seen that expanding the diluent compartment 22 of a multiple compartment container as illustrated in FIGS. 1 and 6 is particularly desirable.

As has been described above, in connection with the embodiment of FIG. 8, the container is confined within a tool having a hollow interior cavity, or cavities, and inflated with a pressurized gas to thereby stretch the material of the container's front and rear sheets (alternatively, the front sheet only) to permanently expand a particular compartment's volumetric capacity. The process and apparatus described in connection with FIGS. 9–13 are equally suitable for use in connection with the multiple compartment container of FIG. 6. All that is required is that the areal footprint of the top and bottom cavities 136 and 138 be reduced, or modified, to conform to the footprint of the diluent compartment 22 of the multiple compartment container 10 of FIG. 6.

The diluent compartment footprint, as that term is used herein, is generally rectangular in shape and is defined, on three sides, by the permanent peripheral seal 16 and, on the fourth side, by the peelable seal 25 which separates the diluent compartment 22 from the medicament compartment 23. Neglecting the channel 41 formed between the diluent compartment 22 and its corresponding sacrificial port 72, the compartment footprint would describe a rectangle which is approximately 3.5 inches wide and approximately 5.0 inches long. Accordingly, the sealing boundary (146 of FIG. 11) is configured and dimensioned to conform to the seal footprint of the diluent compartment 22 of the multiple compartment container of FIGS. 1 and 6.

Because the seal 25 separating the diluent compartment from the medicament compartment is a peelable seal, particular care should be taken to ensure that the sealing boundary (146 of FIG. 11) is configured to lie slightly inside the seals, particularly the peelable seal 55. Recalling that the peelable seal is designed to burst under pressure, it will be recognized that providing the sealing boundary 146 inside the seal footprint and particularly inside the footprint of the peelable seal 55, forms a pressure stop against application of a burst pressure to the peelable seal.

In a manner similar to that described in connection with the embodiment of FIG. 8, the diluent compartment 22 of the multiple compartment container of FIGS. 1 and 6 may be expanded by stretching either the front sheet 12 the rear sheet 14, or both. Because of the characteristics of the films used to form the front and rear sheets, 12 and 14, it will be understood that the front sheet 12 is expandable to a greater degree than the rear sheet 14 under the same time and pressure regime as that described in connection with FIG. 8.

The tool embodiment for use in expanding the diluent compartment of a multiple compartment medical container is generally quite similar to the tool embodiment described in connection with FIGS. 11 and 12. However, because of the smaller areal footprint (3.5 inches×5 inches as opposed to 3.5 inches×7 inches) of the diluent compartment versus the entire container, the depths of the top and bottom cavities 136 and 138 are correspondingly reduced, so as to not over-stretch the diluent compartment film materials. As described above, the bottom cavity 136 has a footprint of approximately 3.5 inches×5 inches and a cavity depth of from about 0.75 inches to about 1.0 inches to define the cavity volume of from about 160 ml to about 175 ml. Preferably, only the front sheet is stretched in the embodiment of FIG. 6, so the top tool portion comprises a substantially flat surface which is not provided with the cavity. However, were a cavity to be provided, it would have a footprint of approximately 3.5 inches×5 inches and a cavity depth of from about 0.25 inches to about 0.35 inches to define the cavity volume of from about 50 ml to about 60 ml. Providing the cavities in such manner, allows the diluent compartment 22 to be expanded from its nominal 50 ml standard capacity to an approximately 100–150 ml volume capacity, as that term has been defined previously.

Once the multiple compartment container of FIGS. 1 and 6 has been disposed with an appropriate inflation tool, the diluent compartment is inflated through its corresponding sacrificial port (72 of FIG. 6) by 0.2 micron filtered air or nitrogen at an inlet pressure of approximately 20 psi. The diluent compartment is maintained in an inflated condition for approximately 15 seconds to allow time for the film to stabilize in its stretched condition. Following volumetric expansion, the multiple compartment container is now ready to be sterilized, aseptically filled, trimmed to its final dimensions and shipped to the ultimate consumer.

Sterilization, Filling and Final Container Formation

Figure 17:
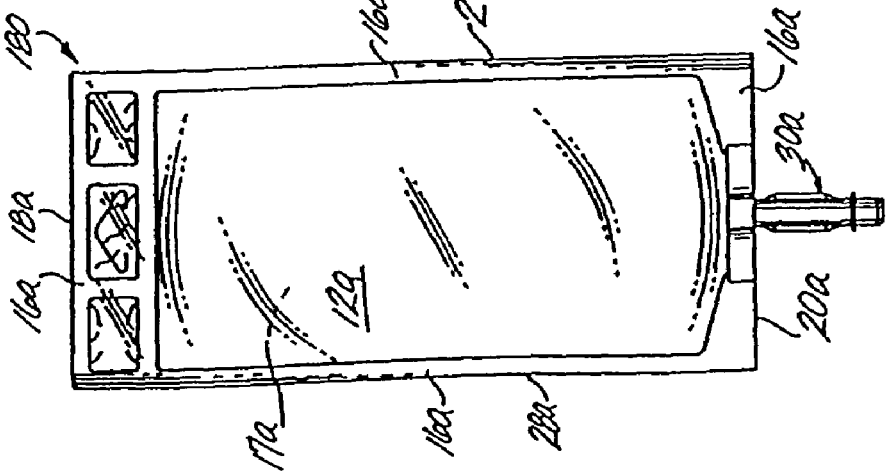
FIG. 17 is a side elevational view of the flexible container of FIG. 8 shown with the sacrificial ports removed and the permanent seal completed along the entire common peripheral edge.

After the container 10a has been enlarged to the desired volume capacity or capacities, it preferably has the configuration exemplified in FIG. 8. The container 10a is now in a condition for sterilization and aseptic filling with a medical solution. After sterilization and filling, the sacrificial ports 72a and 74a may be removed, leaving a finished enlarged container as best illustrated in FIG. 17.

In an exemplary filling process, the particular embodiment of the container to be filled, in accordance with the invention, is one which incorporates a single layer front sheet film 12a and a multi-layer aluminum foil laminate rear sheet film 14a. The front and rear sheets 12a and 14a have been formed to comprise a volume container 17a which has a portion of the common peripheral edge 16a left unsealed for filling through the respectively provided sacrificial ports 72a and 74a. This embodiment of the container 10a at this stage of fabrication is best depicted in FIG. 8. Primary container fabrication, including the provision of an outlet port 30a and sacrificial ports 72a and 74a, is accomplished by the method and apparatus previously described.

In order for an aseptic filling process to be acceptable for medical purposes, the unfilled container 10a must be provided in a sterile condition. Conventionally, container sterilization takes place in a separate processing area or facility due to the rather extensive and complex equipment and processes required for sterilizing material. A particular undesirable feature of the sterilization procedure is that the container must be transported to the sterilization facility for processing, following which container sterility must be maintained during subsequent storage and transport to an aseptic filling facility. The container must be introduced into the aseptic filling zone by means of a sterile transfer in order to prevent contamination of the aseptic zone by the container. Once introduced into the aseptic zone, the container may be filled aseptically, but must be further handled in a sterile fashion.

In accordance with practice of principles of the invention, following primary container fabrication, a plurality of empty containers are loaded into a handling container which is then sealed to protect the flexible containers 10a contained within from environmental contamination.

Turning now to FIG. 14, a transport or handling container, generally indicated at 160 and termed "a carrier" herein, functions as a transportable sterile containment isolator for sterilizing, transporting and introducing into the aseptic zone, empty containers in a systematic manner. The carrier 160 comprises three components; a generally rectangular container tray 162, a sealable film lid 164, and a rail cartridge 166 for supporting a multiplicity of containers 10a within the tray and which will be described in greater detail below. The described carrier 160 is merely an exemplary embodiment and other configurations may also be utilized as will be known to those of skill in the art.

The generally rectangular container tray 162 may be constructed of a thermoformed polystyrene material or other material capable of withstanding several sterilization cycles without significant degradation. The tray 162 may be shaped generally in the form of a basin with its upper peripheral edge bent-over outwardly to form a flat, horizontally oriented peripheral lip or flange 168 which extends beyond the sides of the tray 162 for a distance of between about ¼ inches to about 1 inch. Preferably, the lip 168 extends about ¾ inches beyond the sides of the tray, but any extension which provides rigidity to the tray 162 and a sufficient surface to support a seal is suitable. Two opposing pockets 170 and 172 are formed in about the centers of the two opposing short sides of the tray and extend outward from the plane of the short sides. The pockets 170 and 172 extend only partially downward along the sides of the tray and form, thereby, two opposing recesses into which the ends of the rail cartridge 162 may be inserted. The rail cartridge 166 rests on the bottom surfaces of the pockets 170 and 172 and is thereby suspended above the bottom of the tray 162 at a height sufficient to allow containers 10a arranged on the rail cartridge to hang free within the interior volume of the tray. Accordingly, the pockets 170 and 172, in combination with the rail cartridge 166, functions to maintain a multiplicity of containers 10a in a specific orientation during transport, storage and UV sterilization.

Once the rail cartridge 166 has been loaded with containers 10a and inserted into the pockets 170 and 172, the tray 162 is environmentally sealed by heat sealing the plastic film lid 164 to the tray flange or lip 168 in a distinct orientation. For illustrative purposes in FIG. 14, the film lid 164 is depicted half way through the sealing process, with a portion of the lid lifted up to show the rail cartridge 166 nested within the tray 162. The film lid 164 is positioned on the flange 168 such that there is no "overhang" of the film lid material over the edge of the tray flange around the perimeter of the tray. In an exemplary embodiment, the plastic film lid 164 is constructed to have dimensions which allow the film lid to be positioned on the tray flange 168 such that the film lid edge is inset from the tray flange edge around the entire flange periphery. In addition, the film lid heat seal is applied to extend beyond the edge of the film lid 164, to assure that no portion of the film lid edge left unsealed that would create a loose edge "flap". Film lid orientation, placement and the avoidance of loose edges is particularly important to the surface ultraviolet (UV) decontamination process performed on the carrier 160 when the carrier is introduced to the aseptic zone. Crevices, caused by loose film lid edges and/or flaps, may cause a local shadow, when exposed to UV radiation, which shadowing effect can defeat the UV decontamination process.

Once the film lid 164 has been heat sealed to the tray flange 168, the carrier 160 defines a hermetically sealed environment that functions to isolate its contents from external contamination. The carrier 160 may then be placed into a polybag overwrap or similar covering (not shown), which acts as a "dust cover", and identified with an adhesive label which is placed on the over wrap.

Referring now to FIGS. 15 and 16, a carrier rail cartridge 174 may comprise a plurality of injection molded, polystyrene T-beams 176 disposed at spaced-apart intervals so as to form longitudinally running slots 178 therebetween. Fabricated containers 10a may be loaded onto the cartridge 174. The containers 10a, such as those depicted in FIG. 8, are loaded onto the carrier rail cartridge 166 by inserting their sacrificial ports 72a and 74a into the slots 178 formed between the cartridge's T-rails 176. The T-rails 176 may have edges which are spaced apart a sufficient distance (about 13.0 mm) such that the central filling barrel of each sacrificial port 72a and 74a is able to be accommodated therebetween, and are adapted to engage the sacrificial ports between the port's circumferential flanges (78a and 80a) such that each container 10a is grasped by the T-rail flanges 176 beneath its uppermost circumferential sacrificial port flange 80a.

In the exemplary embodiment of the carrier rail cartridge depicted in FIGS. 15 and 16, four slots 178 are provided for receiving containers 10a, with the containers loaded onto the rail cartridge 166 in alternating left and right orientations. The sacrificial ports 72a and 74a of each container 10a are inserted into two of the slots 178. A first container may be loaded into the second and fourth slots and oriented in a first horizontal direction. A second container may then be loaded onto the rail cartridge 166 with its sacrificial ports 72a and 74a inserted into a first and third cartridge slots 178. The second container 10 is loaded in a second horizontal direction oriented 180° with respect to the first container. Further containers 10a are loaded onto the carrier rail cartridge 166 in like fashion, with the container's horizontal orientation alternating left and right; the sacrificial ports of the left oriented containers inserted into the second and fourth slots, the set ports of the right oriented containers loaded into the first and third slots, as described above, until the carrier rail cartridge 166 is completely filled. Obviously, each carrier will support a larger number of pre-enlarged containers than enlarged containers.

Following loading, the carrier rail cartridge 174 is placed within the tray 162 with the ends of the T-rails 176 nested in the pockets 170 and 172 formed in the ends of the tray. Pockets 170 and 172 support the carrier rail cartridge 166 within the interior volume of the tray and provide additional lateral support which prevents the cartridge from shifting during shipping, sterilization and storage.

The sealed carrier, including the empty containers within, is wrapped in a poly bag or similar container for radiation sterilization where the carrier 160 and the retained containers 10a are rendered sterile by an E-beam sterilization procedure or the like. After the foregoing carrier loading and E-beam sterilization procedure is completed, the sterilized medical containers 10 may be aseptically filled with a medical solution. This may include transporting the carrier 160 and the retained containers 10a to an aseptic filling station. Filling of the volume enclosure 17a may be accomplished using the technique of related co-pending application Ser. No. 08/837,927 filed Apr. 11, 1997, which disclosure is herein fully incorporated by reference. These techniques may be applied to a single medical solution or alternatively to filling multiple compartments.

After sterilization and filling, the fabrication of the enlarged container of FIG. 8 may be completed by removing the sacrificial ports 72a and 74a and completing the permanent seal around the first side 27a of the common peripheral edge 16a. The finished container 180 includes an increased capacity for storing a medical solution relative to a standard or non-enlarged container.

The final fabrication process includes removing a portion of the first side 27a of the container 10a just inward from the sacrificial ports 72a and 74a and including the sacrificial ports. Each of the fluid connections or passageways between the sacrificial ports 72a and 74a and the volume enclosure 17a is then sealed. This is accomplished by applying a permanent seal, similar to that previously described, across the first side 27a just inwardly from the common peripheral edge 16. This permanent seal completes the volume enclosure 17a. When using a multiple compartment container, the permanent seal may be applied across each sacrificial port 72a and 74a after each respective filling. A portion of the first side 27a, including the sacrificial ports 72a and 74a may then be removed. As can be seen relative to the differences between FIG. 8 and FIG. 17, the removed portion includes the sacrificial ports 72a and 74a and a narrow strip of the first side 27a of the container 10a.

Those skilled in the art will recognize that the primary discussion of embodiments comprising a liquid diluent and a single powdered medicament as well as a single volume enclosure embodiment do not limit the scope of the invention. Use of liquid medicaments in the intermediate compartment or a plurality of compartments for powdered and liquid medicaments, to be mixed with the diluent, may be employed using the present invention. Multiple sacrificial ports and communication channels between the sacrificial ports and a respective compartment may easily be provided in accordance with practice of principles of the invention. Moreover, depending on the susceptibility of any of the components comprising the contents of the multiple compartments to moisture or free oxygen contamination, those compartments may be protected by additional applications of a clear, transparent $SiO_x$ containing, high-barrier laminate over the container front sheet in those compartment regions. Such high-barrier laminates may be provided with or without being combined with an aluminum foil containing high-barrier laminate peelable covering.

The above descriptions of exemplary embodiments of flexible, sterile containers are for illustrative purposes. Because of variations which will be apparent to those skilled in the art, the present invention is not intended to be limited to the particular embodiments described above. Such variations, and other modifications and alterations are included within the scope and intent of the invention as described in the following claims.

What is claimed is:

1. A method for forming a flexible container, the method comprising the steps of:
   providing a flexible, transparent front sheet;
   providing a flexible, vapor impermeable rear sheet;
   heating the front and rear sheets in a first localized area to fuse together the heated portions of the adjoining surfaces, thereby forming a permanent seal around a portion of a common peripheral edge of said front and rear sheets, the permanent seal having at least one gap having an opening spaced from the permanent seal for providing a channel between said front and rear sheets; and
   providing at least one sacrificial port interposed between the front and rear sheets and in communication with the channel for aseptically filling the container, the at least one sacrificial port attached to the front and rear sheets by a second seal at the opening of the at least one gap.

2. The method according to claim 1 further comprising the step of heating the front and rear sheets in a second localized area to fuse together the heated portions of the adjoining surfaces, thereby forming a peelable seal extending between two sides of the common peripheral edge, the peelable seal separably joining the front and rear sheets to thereby form a first compartment for containing a first composition and a second compartment for containing a second composition.

3. The method according to claim 2, further comprising the step of providing a second sacrificial port interposed between the front and rear sheets, the at least one and second sacrificial ports in communication with the first and second compartments, respectively.

4. The method according to claim 3 further comprising the steps of:
   aseptically filling the first compartment with a first composition through a respective sacrificial port; and
   aseptically filling the second compartment with a second composition through a respective sacrificial port.

5. The method according to claim 4 further comprising the step of completing the permanent seal along the container's common peripheral edge and removing the sacrificial ports from the container, whereby container formation is completed without being subject to a sterilization step after the compartment filling step.

6. The method according to claim 5, further comprising the step of providing an isolator having a sterile environment, the ambient atmosphere within the isolator maintained in a sterile condition, wherein the first compartment and the second compartment are aseptically filled with pre-sterilized first composition and pre-sterilized second composition in the sterile environment inside the isolator.

7. The method according to claim 6 further comprising the step of sterilizing said container before the first aseptic compartment filling step.

8. The method according to claim 5, wherein said peelable seal is formed by maintaining the heat seal temperature in the range of from 245° F. to 265° F. while applying a pressure in the range of from about 230 psi to about 340 psi for a time in the range of from about 1.5 seconds to about 2.5 seconds.

9. A method for forming a flexible container, the method comprising the steps of:
   providing a flexible, transparent front sheet;
   providing a flexible, vapor impermeable rear sheet;
   heating the front and rear sheets in a first localized area to fuse together the heated portions of the adjoining surfaces, thereby forming a permanent seal around a portion of a common peripheral edge of said front and rear sheets, the permanent seal having at least one gap having an opening spaced from the permanent seal for providing a channel between said front and rear sheets;
   providing at least one sacrificial port interposed between the front and rear sheets and in communication with the channel for aseptically filling the container, the at least one sacrificial port attached to the front and rear sheets by a second seal at the opening of the at least one gap; and
   providing at least one outlet port interposed between the front and rear sheets and attached to the front and rear sheets by the permanent seal.

10. The method as recited in claim 9, further comprising the step of removing the at least one sacrificial port.

11. A method for forming a flexible container, the method comprising the steps of:
   providing a flexible, transparent front sheet comprising a polypropylene-polyethylene co-polymer blended with styrene ethylene-butylene styrene elastomer;
   providing a flexible, vapor impermeable rear sheet;
   heating the front and rear sheets in a first localized area to fuse together the heated portions of the adjoining surfaces, thereby forming a permanent seal around a portion of a common peripheral edge of said front and rear sheets, the permanent seal having at least one gap having an opening spaced from the permanent seal for providing a channel between said front and rear sheets; and
   providing at least one sacrificial port interposed between the front and rear sheets and in communication with the channel for filling the container, the at least one sacrificial port attached to the front and rear sheets by a second seal at the opening of the at least one gap.

12. The method according to claim 11 further comprising the step of heating the front and rear sheets in a second localized area to fuse together the heated portions of the adjoining surfaces, thereby forming a peelable seal extending between two sides of the common peripheral edge, the peelable seal separably joining the front and rear sheets to thereby form a first compartment for containing a first component and a second compartment for containing a second component.

13. The method according to claim 12, wherein the flexible, vapor impermeable rear sheet comprises a multi-layer laminate formed by the steps of:
   providing an inner layer of a polypropylene-polyethylene co-polymer blended with a styrene ethylene-butylene styrene elastomer in an about 80%/20% wt/wt ratio interfacing with the front sheet;
   providing an intermediate layer of aluminum foil; and
   providing an outer thermoplastic layer having a higher melting point than said inner layer.

14. The method according to claim 13, further comprising the step of providing a second sacrificial port interposed between the front and rear sheets, the at least one sacrificial port and the second sacrificial port in communication with the first and the second compartments, respectively.

15. The method according to claim 14, further comprising the step of completing the permanent seal along the container's common peripheral edge and removing the sacrifi cial ports from the container, whereby container formation is completed without being subject to sterilization step.

16. The method according to claim 15, wherein said peelable seal is formed by maintaining the heat seal temperature in the range from 245° F. to 265° F. while applying a pressure in the range of from about 230 psi to about 340 psi for a time in the fange from about 1.5 seconds to about 2.5 seconds.

* * * * *